US012741986B2

(12) United States Patent
Jewett et al.

(10) Patent No.: US 12,741,986 B2
(45) Date of Patent: Sep. 22, 2026

(54) STABLE REACTIVE COMPOSITIONS FOR BIOCONJUGATION, PROBES, AND PROTEIN LABELING

(71) Applicant: ARIZONA BOARD OF REGENTS ON BEHALF OF THE UNIVERSITY OF ARIZONA, Tucson, AZ (US)

(72) Inventors: John C. Jewett, Tucson, AZ (US); Garrett Davis, Tucson, AZ (US); Holly Sofka, Tucson, AZ (US)

(73) Assignee: ARIZONA BOARD OF REGENTS ON BEHALF OF THE UNIVERSITY OF ARIZONA, Tucson, AZ (US)

( * ) Notice: Subject to any disclaimer, the term of this patent is extended or adjusted under 35 U.S.C. 154(b) by 994 days.

(21) Appl. No.: 17/905,787

(22) PCT Filed: Mar. 15, 2021

(86) PCT No.: PCT/US2021/022403
§ 371 (c)(1),
(2) Date: Sep. 7, 2022

(87) PCT Pub. No.: WO2021/184014
PCT Pub. Date: Sep. 6, 2021

(65) Prior Publication Data

US 2023/0111712 A1 Apr. 13, 2023

Related U.S. Application Data

(60) Provisional application No. 62/989,514, filed on Mar. 13, 2020.

(51) Int. Cl.
*C07D 319/06* (2006.01)
*C07K 1/13* (2006.01)
*G01N 33/533* (2006.01)

(52) U.S. Cl.
CPC .............. *C07K 1/13* (2013.01); *C07D 319/06* (2013.01); *G01N 33/533* (2013.01)

(58) Field of Classification Search
CPC ....... C07K 1/13; C07D 319/06; G01N 33/533
See application file for complete search history.

(56) References Cited

U.S. PATENT DOCUMENTS

| | | | | |
|---|---|---|---|---|
| 3,591,575 | A | | 7/1971 | Eugene |
| 3,607,542 | A | | 9/1971 | George et al. |
| 3,959,210 | A | | 5/1976 | Lipatova et al. |
| 4,107,353 | A | | 8/1978 | Gabriel et al. |
| 4,218,279 | A | | 8/1980 | Green |
| 4,356,050 | A | | 10/1982 | Crivello et al. |
| 4,602,073 | A | | 7/1986 | Skoultchi et al. |
| 5,399,697 | A | | 3/1995 | Fobare et al. |
| 5,478,741 | A | * | 12/1995 | Maret .................. C07K 14/445 530/391.1 |
| 5,856,373 | A | | 1/1999 | Kaisaki et al. |
| 8,603,451 | B2 | | 12/2013 | Zhang et al. |
| 8,617,827 | B2 | | 12/2013 | Hell et al. |
| 8,668,978 | B2 | | 3/2014 | Malima et al. |
| 9,085,715 | B2 | | 7/2015 | Berthelot et al. |
| 9,458,143 | B1 | | 10/2016 | Jewett et al. |
| 9,593,080 | B1 | | 3/2017 | Jewett et al. |
| 10,047,061 | B2 | | 8/2018 | Jewett et al. |
| 10,125,105 | B2 | | 11/2018 | Jewett et al. |
| 2002/0197439 | A1 | | 12/2002 | Berneth et al. |
| 2004/0241205 | A1 | | 12/2004 | Babich et al. |
| 2005/0080260 | A1 | | 4/2005 | Mills et al. |
| 2006/0264623 | A1 | | 11/2006 | Smith et al. |
| 2007/0049587 | A1 | | 3/2007 | Zbinden et al. |
| 2007/0098807 | A1 | | 5/2007 | Babich et al. |
| 2007/0104719 | A1 | | 5/2007 | Carter et al. |
| 2009/0048222 | A1 | | 2/2009 | Bell et al. |
| 2009/0286308 | A1 | | 11/2009 | Berthelot et al. |
| 2011/0245287 | A1 | | 10/2011 | Holaday et al. |
| 2012/0035293 | A1 | | 2/2012 | Boydston et al. |
| 2017/0114033 | A1 | | 4/2017 | Jewett et al. |

(Continued)

FOREIGN PATENT DOCUMENTS

| | | | |
|---|---|---|---|
| DE | 265008 | A1 | 2/1989 |
| DE | 4242428 | A1 | 10/1993 |
| WO | 2001081340 | A2 | 11/2001 |
| WO | 2008090554 | A2 | 7/2008 |
| WO | 2009137916 | A1 | 11/2009 |
| WO | 2015073746 | A2 | 5/2015 |
| WO | 2015191735 | A1 | 12/2015 |
| WO | 2017027743 | A1 | 2/2017 |
| WO | 2017180889 | A1 | 10/2017 |
| WO | 2018023130 | A1 | 2/2018 |
| WO | 2018165666 | A1 | 9/2018 |

OTHER PUBLICATIONS

Katharine et al. Click and chemically triggered declick reactions through reversible amine and thiol coupling via a conjugate acceptor. Nature Chemistry 2016, vol. 8, pp. 968-973. (Year: 2016).*
Kimani et al., Water-soluble Triazabutadienes that Release Diazonium Species upon Protonation under Physiologically Relevant Conditions, Angewandte Chemie International Edition, vol. 54, Feb. 6, 2015.
Zhong et al., 2014, Nature Nanotechnology 9, 858-866.
Stewart et al., 2011, J Polym Sci B Polym Phys 49(11):757-771.

(Continued)

*Primary Examiner* — Shafiqul Haq
(74) *Attorney, Agent, or Firm* — NGUYEN TARBET IP LAW

(57) ABSTRACT

Modular Meldrum's acid amine-reactive Michael acceptor (MaMa)—based molecules that are stable probes for high pH environments and bioconjugations. The molecules of the present invention can selectively label and protect lysine residues. In certain embodiments, the molecules can selectively react with lysine at particular pH levels. The probes of the present invention may be used to label proteins in a fluorescent manner, for purification, imaging, or general protein modifications, however the present invention is not limited to the aforementioned applications.

3 Claims, 10 Drawing Sheets

(56) References Cited

U.S. PATENT DOCUMENTS

2017/0320834 A1 11/2017 Regents
2018/0230106 A1 8/2018 Jewett et al.

OTHER PUBLICATIONS

Poulsen et al., 2014, Biofouling 30(4):513-23.
Stewart, 2011, Appl Microbiol Biotechnol 89(1):27-33.
Stewart et al.,, 2011, Adv Colloid Interface Sci 167(1-2):85-93.
Hennebert et al., 2015, Interface Focus 5(1):2014.
Y. Modis, S. Ogata, D. Clements, S. C. Harrison, Nature 2004, 427, 313-319.
C. D. Blanchette, Y. H. Woo, C. Thomas, N. Shen, T. A. Sulchek, A. L. Hiddessen, PLoS One 2009, 4, e6056.
J. Han, K. Burgess, Chem. Rev. 2010, 110, 2709-2728.
J. Kalia, R. T. Raines, Angew. Chem. Int. Ed. Engl. 2008, 47, 7523-7526.
J. Kalia, R. T. Raines, Angew. Chem. 2008, 120, 7633-7636.
J. Z. Du, X. J. Du, C. Q. Mao, J. Wang, J. Am. Chem. Soc. 2011, 133, 17560-17563.
E. H. Cordes, H. G. Bull, Chem. Rev. 1974, 74, 581-603.
A. Luong, T. Issarapanichkit, S. D. Kong, R. Fonga, J. Yang, Org. Biomol. Chem. 2010, 8, 5105-5109.
Fanghänel, R. Hansel, W. Ortmann, J. Hohlfeld, J. Prakt. Chem. 1975, 317, 631-640.
H.-T. Dorsch, H. Hoffmann, R. Hansel, G. Rasch, E. Fanghänel, J. Prakt. Chem. 1976, 318, 671-680.
E. Fanghanel, R. Hänsel, J. Hohlfeld, J. Prakt. Chem. 1977, 319, 485-493.
E. Fanghänel, H. Poleschner, R. Radeglia, R. Hänsel, J. Prakt. Chem. 1977, 319, 813-826.
E. Fanghänel, J. Hohlfeld, J. Prakt. Chem. 1981, 323, 253-261.
R. Radeglia, R. Wolff, T. Steiger, S. Simova, E. Fanghanel, J. Prakt. Chem. 1984, 5, 511-514.
E. Fanghänel, W. Ortmann, A. Hennig, J. Prakt. Chem. 1988, 330, 27-34.
E. Fanghänel, W. Ortmann, J. Prakt. Chem. 1989, 331, 721-725.
E. Fanghänel, J. U. Bauroth, H. Hentschel, F. Gußmann, H. Alzyadi, W. Ortmann, J. Prakt.Chem. 1992, 334, 241-247.
D. M. Khramov, C. W. Bielawski, Chem. Commun. 2005, 4958-4960.
S. Dahmen, S. Brase, Org. Lett. 2000, 2, 3563-3565.
S. Brase, Acc. Chem. Res. 2004, 37, 805-816.
D. Jishkariani, C. D. Hall, A. Demircan, B. J. Tomlin, P. J. Steel, A. R. Katritzky, J. Org. Chem. 2013, 78, 3349-3354.
D. M. Khramov, C. W. Bielawski, J. Org. Chem. 2007, 72, 9407-9417.
A. G. Tennyson, E. J. Moorhead, B. L. Madison, J. A. V. ER, V. M. Lynch, C. W. Bielawski, Eur. J. Org. Chem. 2010, 6277-6282.
W. Herrmann, C. Kocher, Angew. Chem. Int. Ed. 1997, 36, 2162-2187.
N. Marion, S. Díez-González, S. P. Nolan, Angew. Chem. Int. Ed. Engl. 2007, 46, 2988-3000.
A. F. Hegarty, in The Chemistry of Diazonium and Diazo Groups, vol. 2 (Ed.: S. Patai), John Wiley & Sons, Ltd., New York, NY, 1978, pp. 511-591.
L. P. Hammett, J. Am. Chem. Soc. 1937, 59, 96-103.
B. M. Tracey, D. E. G. Shuker, Chem. Res. Toxicol. 1997, 10, 1378-1386.
J. M. Hooker, E. W. Kovacs, M. B. Francis, J. Am. Chem. Soc. 2004, 126, 3718-3719.
J. Gavrilyuk, H. Ban, M. Nagano, W. Hakamata, C. F. Barbasiii, Bioconjugate Chem. 2012, 23, 2321-2328.
L. Wang, V. Gruzdys, N. Pang, F. Meng, X.-L. Sun, RSC Adv. 2014, 4, 39446.
European Journal of Inorganic Chemistry vol. 2013, Issue 12, p. 2020-2030, Apr. 2013 Elena García-Moreno, Elena Cerrada, M. José Bolsa, Asunción Luquin and Mariano Laguna.
European Journal of Medicinal Chemistry vol. 46, Issue 7, Jul. 2012, p. 2748-2758, Marijana Hranjeca, Borka Lučicá, Ivana Ratkajb, Sandra Kraljević Pavelićb, Ivo Piantanidac, Krešimir Pavelićb, Grace Karminski-Zamola.
Phosphate-buffered saline (PBS) CSH Protocols. "http://cshprotocols.cshlp.org/content/2006/1/pdb.rec8247".
Cornaii, 'Development of Clickable Triazabutadienes as Cleavable Cross-linkers', A thesis submitted to the Faculty of the Department of Chemistry and Biochemistry In Partial Fulfillment of the Requirements For the Degree of Master of Science, The University of Arizona, Apr. 8, 2016.
Pubchem, SID 42688522, Decemeber 05, 2007 [retrieved on Nov. 18, 2016].
Guzman et al. Protecting Triazabutadienes to Afford Acid Resistance, ChemBioChem Sep. 23, 2016. vol. 17, p. 2220-2222.
Arlett, J. L., Myers, E. B., & Roukes, M. L. (2011). Comparative advantages of mechanical biosensors. Nature Nanotechnology, 6(4), 203-215. http://doi.org/10.1038/nnano.2011.44.
Gooding, J. J., & Darwish, N. (2012). The rise of self-assembled monolayers for fabricating electrochemical biosensors-an interfacial perspective. Chemical Record, 12(1), 92-105. http://doi.org/10.1002/tcr.201100013.
Grieshaber, D., Mackenzie, R., Vörös, J., & Reimhult, E. (2008). Electrochemical Biosensors—Sensor Principles and Architectures. Sensors, 8(3), 1400-1458. http://doi.org/10.3390/s8031400.
Gwent Systems, G. A. M. (n.d.). Electrochemical Biosensor Materials. Retrieved from http://www.gwent.org/presentations/biosensors.pdf.
Jung, J., & Lim, S. (2013). ZnO nanowire-based glucose biosensors with different coupling agents. Applied Surface Science, 265, 24-29. http://doi.org/10.1016/j.apsusc.2012.10.069.
Mahouche-Chergui, S., Gam-Derouich, S., Mangeney, C., & Chehimi, M. M. (2011). Aryl diazonium salts: a new class of coupling agents for bonding polymers, biomacromolecules and nanoparticles to surfaces. Chemical Society Reviews, 40(7), 4143-4166. http://doi.org/10.1039/c0cs00179a.
Reyes De Corcuera, J., & Cavalieri, R. (2003). Biosensors. Encyclopedia of Agricultural, Food, and Biological Engineering, 119-123. http://doi.org/10.1081/E-EAFE.
Smith, R. K., Lewis, P. A., & Weiss, P. S. (2004). Patterning self-assembled monolayers. Progress in Surface Science, 75(1-2), 1-68. http://doi.org/10.1016/j.progsurf.2003.12.001.
Thévenot, D. R., Toth, K., Durst, R. A., & Wilson, G. S. (2001). Electrochemical biosensors: Recommended definitions and classification. Biosensors and Bioelectronics, 16(1-2), 121-131. http://doi.org/10.1016/S0956-5663(01)00115-4.
Addy et al. 'A Chemoselective Rapid Azo-Coupling Reaction (CRACR) for "Unclickable" Bioconjugation', J Am Chem Soc. 2017, vol. 139(34), pp. 11670-11673. doi:10.1021/jacs.7b05125.
Jensen et at 'Light-Activated Triazabutadienes for the Modification of a Viral Surface', Chembiochem. 2016, vol. 17 (23), pp. 2216-2219. doi:10.1002/cbic.20160050B.
Gupta et al. "Profiling the reactivity of cyclic C-nucleophiles towards electrophilic sulfur in cysteine sulfenic acid." Chemical science 7.1 (2016): 400-415.
Dorwald, Florencio Zaragoza. Side reactions in Organic Synthesis: a guide to successful synthesis design. John Wiley & Sons, 2006. Preface.
Khramov et al. "Triazene formation via reaction of imidazol-2-ylidenes with azides." Chemical communications 39 (2005): 4958-4960.
Lippert, Th, et al. "Photolysis of 1-aryl-3, 3-dialkytriazenes." Journal of Photochemistry and Photobiology A: Chemistry 78.2 (1994): 139-148.
Amoroso, Jon William. Reactive Probes for Manipulating Polyketide Synthases, and Photoreactive Probes for Strained Alkyne Click Chemistry. University of Massachusetts Amherst, 2014.
National Center for Biotechnology Information (2022). PubChem Substance Record for SID 355052434, 2-(piperidin-1-yldiazenyl)benzoic acid, Source: Springer Nature. Retrieved Nov.

(56) References Cited

OTHER PUBLICATIONS 16, 2022 from https://pubchem.ncbi.nlm.nih.gov/substance/355052434.

* cited by examiner 1 2 3 4 5

*Present Invention*

*Formula A* *Formula B*

*Present Invention with lysine*

2 3

4/5 a

4/5 b

R =

4

5

(4a)

*PEG-Azide MaMa*

*PEG-Azide control* (4b)

(5a)

*NBD MaMa*

(5b) *NBD MaMa control*

6

R = a or b (9)

Click Ready (4)

Fluorescent (10)

(7)

(8)

(7)

BHQ (11)

(12)

(13)

(14)

(15)

(16)

(17)

(18)

(19)

(20)

(21)

(22)

(23)

(24)

(25)

(26)

(27)

(28)

(29)

(30)

STABLE REACTIVE COMPOSITIONS FOR BIOCONJUGATION, PROBES, AND PROTEIN LABELING

CROSS-REFERENCES TO RELATED APPLICATIONS

This application claims benefit of U.S. Provisional Patent Application No. 62/989,514 filed Mar. 13, 2020, the specification(s) of which is/are incorporated herein in their entirety by reference.

STATEMENT REGARDING FEDERALLY SPONSORED RESEARCH OR DEVELOPMENT

This invention was made with government support under Grant Nos. 1552568 awarded by National Science Foundation and T32 GM008804 awarded by National Institutes of Health. The government has certain rights in the invention.

BACKGROUND OF THE INVENTION

Field of the Invention

The present invention relates to molecules, conjugates, and probes for labeling proteins or other molecules of interest, more particularly to molecules, conjugates, and probes that can selectively react with lysine.

Background Art

Protein bioconjugation techniques are critical to multiple areas of investigation, including but not limited to probing solvent exposed protein structures for biophysical characterization, or attaching antibodies to imaging agents or cytotoxic drugs.

Inventors surprisingly discovered that an amine can be added twice to a Meldrum's acid derivative in an aqueous solution, despite the belief in the art that a second amine could not be added in any appreciable amount (Diehl et al., 2016, Nature Chemistry 8:968-973) (see FIG. 1).

The present invention describes modular Meldrum's acid amine-reactive Michael acceptors (herein referred to as "MaMa" molecules, probes, or compounds, or MaMas," see Formula A in FIG. 1) that are amine-reactive probes (e.g., lysine-reactive probes), forming a double amine adduct (see Formula B of FIG. 1). The MaMa molecules described herein are pH responsive. For example, the MaMa molecules of the present invention can react with lysine or other amines in high pH levels, e.g., a pH level above 7, e.g., a pH of 8, 9, 10, etc. However, the present invention is not limited to a pH level above 7. The environment or conditions, e.g., the pH of the aqueous solution or the microenvironment of the molecule, that favor the double amine addition reaction is dependent upon the $pK_a$ of the MaMa molecule (electrophile) as well as the $pK_a$ of the amine (nucleophile). For example, the MaMa molecule may react with an amine (e.g., lysine) in an aqueous solution that does not necessarily have a high pH if the local environment of the MaMa molecule and amine is favorable, e.g., if the local environment is such that the amine and MaMa molecule are both in their active forms. A non-limiting example of a microenvironment includes an active site of a molecule. Without wishing to limit the present invention to any theory or mechanism, it is believed that this property may provide for increased reaction specificity.

Once the MaMa molecules form the double amine adducts, the molecules (the double amine molecules) are markedly stable. For example, the double amine molecules may be stable in the presence of nucleophiles (e.g., DTT, cysteine) and may be water stable across a wide pH range (e.g., a pH from 2-12).

As discussed, the MaMa molecules described herein may be used for a variety of purposes, such as probes, bioconjugation applications, etc.

Without wishing to limit the present invention to any theory or mechanism, it is believed that the MaMa molecules of the present invention are advantageous over prior art lysine-reactive probes, such as N-hydroxysuccinimide (NHS) esters, which are not hydrolytically stable, or isothiocyanates, whose synthesis can suffer from functional group incompatibility and have limited utility.

BRIEF SUMMARY OF THE INVENTION

As used herein, the term "Meldrum's acid amine-reactive Michael acceptor" (MaMa) refers to a molecule based on a Meldrum's acid derivative with an amine substitution replacing a thiol, e.g., MaMa compositions according to Formula A below (see also FIG. 1). In some embodiments, SR' is methane thiol (SMe); however, the present invention is not limited to methane thiol.

Formula A

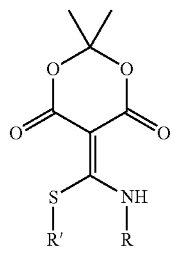

The MaMa compounds of the present invention, e.g., according to Formula A, can react with amines (e.g., lysine) and undergo substitution chemistry whereby the thiol SR' is eliminated from the molecule. This yields compositions according to Formula B below (see also FIG. 1).

Formula B

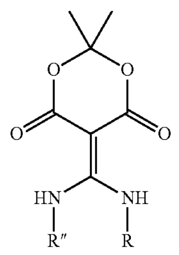

The present invention also provides various analogs comprising a variety of functional moieties such as but not limited to fluorophores and bio-orthogonal handles, including azides, alkynes, tetrazines, strained alkenes, etc. The molecules or compositions of the present invention may be used to label proteins for fluorescence, for purification, imaging, surface immobilization, conjugation to other species to add functionality, or general protein modifications. For example, the present invention provides an analog that is fluorogenic and can be used for live imaging in biological systems. The molecules herein can be used to prepare a protein for purification, e.g., link a purification-associated tag or linker to the protein of interest.

The present invention provides a kit comprising: a composition according to Formula A in aqueous solution; and a set of instructions or access thereto that provides a method for reacting the composition according to Formula A with an amine to produce a double amine adduct (e.g., a composition according to Formula B).

The present invention also features a kit comprising a composition according to Formula A, wherein the composition is a solid; and a set of instructions or access thereto that provides a method for reacting the composition according to Formula A with an amine to produce a double amine composition, e.g., a composition according to Formula B. In certain embodiments, the kit further comprises an aqueous solution for dissolving the composition.

Referring to any of the embodiments herein, e.g., the aforementioned kits, compositions, methods, etc., the present invention is not limited to physically printed instructions packaged with the composition, e.g., packaged together physically within the kit. The instructions may be communicated to the user separately from the physical packaging. For example, “access” to the instruction may refer to verbal communication or written communication external to the packaging of the kit. A non-limiting example of access to the instructions may include access to a website. However, the present invention is not limited to website access to the instructions.

The kit may further comprise a reaction solution. In certain embodiments, the reaction solution raises the pH of the aqueous solution. In certain embodiments, the reaction solution is for reacting the composition according to Formula A with the amine.

In certain embodiments, the aqueous solution has a neutral pH, e.g., from 6.5 to 7.5. In certain embodiments, the aqueous solution has a pH of 7 or greater. In certain embodiments, the aqueous solution has a pH of 8 or greater. In certain embodiments, the aqueous solution has a pH of 9 or greater. In certain embodiments, the aqueous solution has a pH of 10 or greater. In certain embodiments, the aqueous solution has a pH of that is within 20% of a $pK_a$ of —NH of Formula A. In certain embodiments, the aqueous solution has a pH of that is within 10% of a $pK_a$ of —NH of Formula A.

In certain embodiments, the composition forms a hydroxylate intermediate. In certain embodiments, the composition is stable for at least 1 month. In certain embodiments, the composition is stable for at least 6 months. In certain embodiments, the composition is stable at room temperature.

Referring to any of the embodiments herein, R may be a bioorthogonal molecule. In some embodiments, R is an amino acid. The amino acid may be part of a peptide. In certain embodiments, R is a fluorophore, e.g., rhodamine, a fluorescein derivative, TAMRA, BDP, Cyanine3, Cyanine 5, Cyanine 7, a cadaverine derivative, a putrescin derivative, an AlexaFluor dye, or a DynaFluor dye. In certain embodiments, R is selected from: an azide, a terminal alkyne, a cyclic (strained) alkyne, a strained alkene, or a tetrazine. In certain embodiments, R is a label or tag. In certain embodiments, R is a pull-down handle. In certain embodiments, R is biotin or a biotin derivative. In certain embodiments, the tag is selected from: a His tag, a FLAG tag, a Myc tag, a GST tag, an HA tag, an AviTag, a Strep tag, a V5 tag, and ALFA tag, a Spot tag, a T7 tag, an NE tag, a C tag, a calmodulin tag, a polyglutamate tag, a polyarginine tag, an E tag, a Rho tag, an S tag, an SBP tag, a Softag tag, a TC tag, a Ty tag, a VSV tag, an Xpress tag, a SNAP tag, a CLIP tag, a Halo tag, a BCCP tag, a glutathione transferase tag, a GFP tag, an HUH tag, a maltose binding protein tag, a Nus tag, a thioredoxin tag, an Fc tag, a CRDSAT tag, an imaging tag, and a mass tag. In certain embodiments, the label is a quantum dot. In certain embodiments, R is a DNA molecule. The DNA molecule may be part of an oligonucleotide. In certain embodiments, R is an RNA molecule. The RNA molecule may be part of an oligonucleotide. In certain embodiments, R is a cellular localization moiety. In certain embodiments, R is a drug. In certain embodiments, R is a protein drug conjugate. In certain embodiments, R is a cytotoxic molecule. In certain embodiments, R is a protein fluorophore conjugate. In certain embodiments, R is polyethylene glycol (PEG) or a substituted PEG. In certain embodiments, the bioorthogonal handle is a PEG-linked variant of an azide, a terminal alkyne, a cyclic (strained) alkyne, a strained alkene, a tetrazine, a biotin-derivative, a peptide, or a combination thereof. In certain embodiments, R is a solid support. The solid support may be for protein purification or other purposes. In certain embodiments, the solid support is for surface plasmon resonance (SPR). In certain embodiments, the solid support is a resin. In certain embodiments, the solid support is a plate. In certain embodiments, the solid support is a slide.

Referring to any of the embodiments herein, in certain embodiments, R' is selected from $—CH_3$ or $—(CH_2)_nCH_3$. In certain embodiments, R' is a fluorophore. In certain embodiments, R' is a cellular localization moiety. In certain embodiments, R' is label or tag. In certain embodiments, R' is a fluorescence quencher. In certain embodiments, R' is a drug. In certain embodiments, R is a fluorophore and R' is a quencher.

In certain embodiments, the kit further comprises a reaction solution. In certain embodiments, the kit further comprises a quenching buffer. In certain embodiments, the quenching buffer comprises a nucleophilic amine. In certain embodiments, the quenching buffer comprises Tris.

In certain embodiments, the kit further comprises a surface of solid support. In certain embodiments, the kit further comprises instructions or access thereto for attaching the composition to the solid support.

The present invention also features a composition comprising Formula A in an aqueous solution having a pH of 8 or greater. The present invention also features a composition comprising Formula A in an aqueous solution having a pH of 9 or greater. The present invention also features a composition comprising Formula A in an aqueous solution having a pH of 10 or greater. The present invention also features a composition comprising Formula A in an aqueous solution having a pH of 11 or greater. The present invention also features a composition comprising Formula A in an aqueous solution having a pH of 12 or greater. The present invention also features a composition comprising Formula A in an aqueous solution, wherein R is a bioorthogonal functional group.

Referring to any of the embodiments herein, e.g., the aforementioned kits, compositions, methods, etc., in certain embodiments, the aqueous solution has a neutral pH, e.g., from 6.5 to 7.5. In certain embodiments, the aqueous solution has a pH of 7 or greater. In certain embodiments, the aqueous solution has a pH of 8 or greater. In certain embodiments, the aqueous solution has a pH of 9 or greater. In certain embodiments, the aqueous solution has a pH of 10 or greater. In certain embodiments, the aqueous solution has a pH of that is within 20% of a $pK_a$ of —NH of Formula A. In certain embodiments, the aqueous solution has a pH of that is within 10% of a $pK_a$ of —NH of Formula A.

In certain embodiments, the composition forms a hydroxylate intermediate. In certain embodiments, the composition is stable for at least 1 month. In certain embodiments, the composition is stable for at least 6 months. In certain embodiments, the composition is stable at room temperature.

Referring to any of the embodiments herein, R may be a bioorthogonal molecule. In some embodiments, R is an amino acid. The amino acid may be part of a peptide. In certain embodiments, R is a fluorophore, e.g., rhodamine, a fluorescein derivative, TAMRA, BDP, Cyanine3, Cyanine 5, Cyanine 7, a cadaverine derivative, a putrescin derivative, an AlexaFluor dye, or a DynaFluor dye. In certain embodiments, R is selected from: an azide, a terminal alkyne, a cyclic (strained) alkyne, a strained alkene, or a tetrazine. In certain embodiments, R is a label or tag. In certain embodiments, R is a pull-down handle. In certain embodiments, R is biotin or a biotin derivative. In certain embodiments, the tag is selected from: a His tag, a FLAG tag, a Myc tag, a GST tag, an HA tag, an AviTag, a Strep tag, a V5 tag, and ALFA tag, a Spot tag, a T7 tag, an NE tag, a C tag, a calmodulin tag, a polyglutamate tag, a polyarginine tag, an E tag, a Rho tag, an S tag, an SBP tag, a Softag tag, a TC tag, a Ty tag, a VSV tag, an Xpress tag, a SNAP tag, a CLIP tag, a Halo tag, a BCCP tag, a glutathione transferase tag, a GFP tag, an HUH tag, a maltose binding protein tag, a Nus tag, a thioredoxin tag, an Fc tag, a CRDSAT tag, an imaging tag, and a mass tag. In certain embodiments, the label is a quantum dot. In certain embodiments, R is a DNA molecule. The DNA molecule may be part of an oligonucleotide. In certain embodiments, R is an RNA molecule. The RNA molecule may be part of an oligonucleotide. In certain embodiments, R is a cellular localization moiety. In certain embodiments, R is a drug. In certain embodiments, R is a protein drug conjugate. In certain embodiments, R is a cytotoxic molecule. In certain embodiments, R is a protein fluorophore conjugate. In certain embodiments, R is polyethylene glycol (PEG) or a substituted PEG. In certain embodiments, the bioorthogonal handle is a PEG-linked variant of an azide, a terminal alkyne, a cyclic (strained) alkyne, a strained alkene, a tetrazine, a biotin-derivative, a peptide, or a combination thereof. In certain embodiments, R is a solid support. The solid support may be for protein purification or other purposes. In certain embodiments, the solid support is for surface plasmon resonance (SPR). In certain embodiments, the solid support is a resin. In certain embodiments, the solid support is a plate. In certain embodiments, the solid support is a slide.

Referring to any of the embodiments herein, in certain embodiments, R' is selected from $-CH_3$ or $-(CH_2)_nCH_3$. In certain embodiments, R' is a fluorophore. In certain embodiments, R' is a cellular localization moiety. In certain embodiments, R' is label or tag. In certain embodiments, R' is a fluorescence quencher. In certain embodiments, R' is a drug. In certain embodiments, R is a fluorophore and R' is a quencher.

The present invention also features a system comprising a surface bound with a composition according to Formula A. The present invention also features a system comprising a surface bound with a composition according to Formula A and a set of instructions or access thereto that provides a method for reacting the composition according to Formula A with an amine to produce a double amine adduct.

In certain embodiments, the system is for capturing proteins. In certain embodiments, the system is for protein purification. In certain embodiments, the system is for surface plasmon resonance (SPR). In certain embodiments, the surface is a resin. In certain embodiments, the surface is a plate. In certain embodiments, the surface is a slide.

In certain embodiments, the composition forms a hydroxylate intermediate. In certain embodiments, the composition is stable for at least 1 month. In certain embodiments, the composition is stable for at least 6 months. In certain embodiments, the composition is stable at room temperature.

Referring to any of the embodiments herein, R may be a bioorthogonal molecule. In some embodiments, R is an amino acid. The amino acid may be part of a peptide. In certain embodiments, R is a fluorophore, e.g., rhodamine, a fluorescein derivative, TAMRA, BDP, Cyanine3, Cyanine 5, Cyanine 7, a cadaverine derivative, a putrescin derivative, an AlexaFluor dye, or a DynaFluor dye. In certain embodiments, R is selected from: an azide, a terminal alkyne, a cyclic (strained) alkyne, a strained alkene, or a tetrazine. In certain embodiments, R is a label or tag. In certain embodiments, R is a pull-down handle. In certain embodiments, R is biotin or a biotin derivative. In certain embodiments, the tag is selected from: a His tag, a FLAG tag, a Myc tag, a GST tag, an HA tag, an AviTag, a Strep tag, a V5 tag, and ALFA tag, a Spot tag, a T7 tag, an NE tag, a C tag, a calmodulin tag, a polyglutamate tag, a polyarginine tag, an E tag, a Rho tag, an S tag, an SBP tag, a Softag tag, a TC tag, a Ty tag, a VSV tag, an Xpress tag, a SNAP tag, a CLIP tag, a Halo tag, a BCCP tag, a glutathione transferase tag, a GFP tag, an HUH tag, a maltose binding protein tag, a Nus tag, a thioredoxin tag, an Fc tag, a CRDSAT tag, an imaging tag, and a mass tag. In certain embodiments, the label is a quantum dot. In certain embodiments, R is a DNA molecule. The DNA molecule may be part of an oligonucleotide. In certain embodiments, R is an RNA molecule. The RNA molecule may be part of an oligonucleotide. In certain embodiments, R is a cellular localization moiety. In certain embodiments, R is a drug. In certain embodiments, R is a protein drug conjugate. In certain embodiments, R is a cytotoxic molecule. In certain embodiments, R is a protein fluorophore conjugate. In certain embodiments, R is polyethylene glycol (PEG) or a substituted PEG. In certain embodiments, the bioorthogonal handle is a PEG-linked variant of an azide, a terminal alkyne, a cyclic (strained) alkyne, a strained alkene, a tetrazine, a biotin-derivative, a peptide, or a combination thereof.

Referring to any of the embodiments herein, in certain embodiments, R' is selected from $-CH_3$ or $-(CH_2)_nCH_3$. In certain embodiments, R' is a fluorophore. In certain embodiments, R' is a cellular localization moiety. In certain embodiments, R' is label or tag. In certain embodiments, R' is a fluorescence quencher. In certain embodiments, R' is a drug. In certain embodiments, R is a fluorophore and R' is a quencher.

The present invention also features a method of producing a composition according to Formula B. In certain embodiments, the method comprises: in an aqueous solution, introducing an amine to a composition according to Formula A, wherein the composition according to Formula A reacts with the amine to form a composition according to Formula B.

In certain embodiments, the amine is that of a lysine molecule. The lysine molecule may be an amino acid of a protein. In certain embodiments, the aqueous solution has a pH that is within 20% of a $pK_a$ of the composition according to Formula A and within 20% of a $pK_a$ of the amine. In certain embodiments, the aqueous solution has a pH that is within 10% of a $pK_a$ of the composition according to Formula A and within 10% of a $pK_a$ of the amine. In certain embodiments, the aqueous solution has a pH that is 8 or greater. In certain embodiments, the aqueous solution has a pH that is 9 or greater. In certain embodiments, the aqueous solution has a pH that is 10 or greater. In certain embodiments, the composition according to Formula B is produced within 1 hour. In certain embodiments, the composition according to Formula B is produced within 2 hours. In certain embodiments, the composition according to Formula B is produced within 6 hours.

The present invention also features a method of labelling a protein. In certain embodiments, the method comprises: introducing to the protein a composition according to Formula A, wherein the composition reacts with and binds to a lysine residue of the protein. The present invention also features a method of preparing a protein for purification. In certain embodiments, the method comprises: introducing to the protein a composition according to Formula A, wherein R comprises a purification-associated tag, wherein the composition reacts with and binds to lysine residues of the protein, thereby attaching the purification associated tag to the protein. The present invention also features a method of preparing a protein for imaging. In certain embodiments, the method comprises introducing to the protein a composition according to Formula A, wherein R comprises an imaging associated tag, wherein the composition reacts with and attaches to lysine residues of the protein, thereby attaching the imaging associated tag with the protein. The imaging may be live imaging in a biological system. The present invention also features a method of capturing proteins. In certain embodiments, the method comprises applying a protein in solution to a system, the system comprising a surface bound with a composition according to Formula A, wherein the protein reacts with and binds to the composition according to Formula A that is bound to the surface, thereby linking the protein to the surface.

Referring to any of the embodiments herein, e.g., the aforementioned methods, R may be a bioorthogonal molecule. In some embodiments, R is an amino acid. The amino acid may be part of a peptide. In certain embodiments, R is a fluorophore, e.g., rhodamine, a fluorescein derivative, TAMRA, BDP, Cyanine3, Cyanine 5, Cyanine 7, a cadaverine derivative, a putrescin derivative, an AlexaFluor dye, or a DynaFluor dye. In certain embodiments, R is selected from: an azide, a terminal alkyne, a cyclic (strained) alkyne, a strained alkene, or a tetrazine. In certain embodiments, R is a label or tag. In certain embodiments, R is a pull-down handle. In certain embodiments, R is biotin or a biotin derivative. In certain embodiments, the tag is selected from: a His tag, a FLAG tag, a Myc tag, a GST tag, an HA tag, an AviTag, a Strep tag, a V5 tag, and ALFA tag, a Spot tag, a T7 tag, an NE tag, a C tag, a calmodulin tag, a polyglutamate tag, a polyarginine tag, an E tag, a Rho tag, an S tag, an SBP tag, a Softag tag, a TC tag, a Ty tag, a VSV tag, an Xpress tag, a SNAP tag, a CLIP tag, a Halo tag, a BCCP tag, a glutathione transferase tag, a GFP tag, an HUH tag, a maltose binding protein tag, a Nus tag, a thioredoxin tag, an Fc tag, a CRDSAT tag, an imaging tag, and a mass tag. In certain embodiments, the label is a quantum dot. In certain embodiments, R is a DNA molecule. The DNA molecule may be part of an oligonucleotide. In certain embodiments, R is an RNA molecule. The RNA molecule may be part of an oligonucleotide. In certain embodiments, R is a cellular localization moiety. In certain embodiments, R is a drug. In certain embodiments, R is a protein drug conjugate. In certain embodiments, R is a cytotoxic molecule. In certain embodiments, R is a protein fluorophore conjugate. In certain embodiments, R is polyethylene glycol (PEG) or a substituted PEG. In certain embodiments, the bioorthogonal handle is a PEG-linked variant of an azide, a terminal alkyne, a cyclic (strained) alkyne, a strained alkene, a tetrazine, a biotin-derivative, a peptide, or a combination thereof.

Referring to any of the embodiments herein, in certain embodiments, R' is selected from $—CH_3$ or $—(CH_2)_nCH_3$. In certain embodiments, R' is a fluorophore. In certain embodiments, R' is a cellular localization moiety. In certain embodiments, R' is label or tag. In certain embodiments, R' is a fluorescence quencher. In certain embodiments, R' is a drug. In certain embodiments, R is a fluorophore and R' is a quencher.

The present invention also features a composition according to Formula B in an aqueous solution. The present invention also features a composition according to Formula B in an aqueous solution having a pH from 2-5. The present invention also features a composition according to Formula B in an aqueous solution having a pH from 5-8. The present invention also features a composition according to Formula B in an aqueous solution having a pH from 7-12.

In certain embodiments, R" is a lysine molecule. In certain embodiments, the lysine is an amino acid of a protein. In certain embodiments, the lysine is a derivative of lysine. In certain embodiments, the derivative of lysine is a non-naturally occurring amino acid.

In certain embodiments, the composition forms a hydroxylate intermediate. In certain embodiments, the composition is stable for at least 1 month. In certain embodiments, the composition is stable for at least 6 months. In certain embodiments, the composition is stable at room temperature.

Referring to any of the embodiments herein, R may be a bioorthogonal molecule. In some embodiments, R is an amino acid. The amino acid may be part of a peptide. In certain embodiments, R is a fluorophore, e.g., rhodamine, a fluorescein derivative, TAMRA, BDP, Cyanine3, Cyanine 5, Cyanine 7, a cadaverine derivative, a putrescin derivative, an AlexaFluor dye, or a DynaFluor dye. In certain embodiments, R is selected from: an azide, a terminal alkyne, a cyclic (strained) alkyne, a strained alkene, or a tetrazine. In certain embodiments, R is a label or tag. In certain embodiments, R is a pull-down handle. In certain embodiments, R is biotin or a biotin derivative. In certain embodiments, the tag is selected from: a His tag, a FLAG tag, a Myc tag, a GST tag, an HA tag, an AviTag, a Strep tag, a V5 tag, and ALFA tag, a Spot tag, a T7 tag, an NE tag, a C tag, a calmodulin tag, a polyglutamate tag, a polyarginine tag, an E tag, a Rho tag, an S tag, an SBP tag, a Softag tag, a TC tag, a Ty tag, a VSV tag, an Xpress tag, a SNAP tag, a CLIP tag, a Halo tag, a BCCP tag, a glutathione transferase tag, a GFP tag, an HUH tag, a maltose binding protein tag, a Nus tag, a thioredoxin tag, an Fc tag, a CRDSAT tag, an imaging tag, and a mass tag. In certain embodiments, the label is a quantum dot. In certain embodiments, R is a DNA molecule. The DNA molecule may be part of an oligonucleotide. In certain embodiments, R is an RNA molecule. The RNA molecule may be part of an oligonucleotide. In certain embodiments, R is a cellular localization moiety. In certain embodiments, R is a drug. In certain embodiments, R is a protein drug conjugate. In certain embodiments, R is a cytotoxic molecule. In certain embodiments, R is a protein fluorophore conjugate. In certain embodiments, R is polyethylene glycol (PEG) or a substituted PEG. In certain embodiments, the bioorthogonal handle is a PEG-linked variant of an azide, a terminal alkyne, a cyclic (strained) alkyne, a strained alkene, a tetrazine, a biotin-derivative, a peptide, or a combination thereof. In certain embodiments, R is a solid support. The solid support may be for protein purification or other purposes. In certain embodiments, the solid support is for surface plasmon resonance (SPR). In certain embodiments, the solid support is a resin. In certain embodiments, the solid support is a plate. In certain embodiments, the solid support is a slide.

Any feature or combination of features described herein are included within the scope of the present invention provided that the features included in any such combination are not mutually inconsistent as will be apparent from the context, this specification, and the knowledge of one of ordinary skill in the art. Additional advantages and aspects of the present invention are apparent in the following detailed description and claims.

BRIEF DESCRIPTION OF THE SEVERAL VIEWS OF THE DRAWING(S)

The features and advantages of the present invention will become apparent from a consideration of the following detailed description presented in connection with the accompanying drawings in which:

FIG. 1 shows Formula A and Formula B of the present invention relative to the prior art (Diehl et al., 2016, Nature Chemistry 8:968-973). The prior art illustrates conjugation of an amine to the conjugate acceptor, followed by release of the amine upon addition of DTT. The present invention describes a second amine addition to Formula A (e.g., second amine addition in an aqueous solution at pH >9) as a stable bioconjugation to create Formula B. FIG. 1 also shows a non-limiting example of a compound according to Formula A reacting with lysine to create a stable double amine conjugate. The present invention is not limited to the reaction conditions in FIG. 1.

FIG. 2 shows the schematic conversion of the single amine adduct (2) (MaMa molecule) to the double amine adduct (3) (double amine molecule) used to measure the kinetics of the second addition. The concentration of (2) relative to the conversion of (2) to (3) at various pH (7-10) over the course of 60 minutes is shown.

FIG. 3 shows the equilibrium of the single amine adduct existing in the active neutral form and the unreactive anionic form upon deprotonation, as well as the equilibrium of propyl amine in its unreactive protonated form and its nucleophilic neutral form. FIG. 3 also shows a plot of the relative reactive species of the neutral single amine adduct and the neutral propyl amine as a function of pH, overlaid with an optimal reactivity curve. The present invention is not bound by any theory related to the optimal reactivity curve.

DETAILED DESCRIPTION OF THE INVENTION

The present invention provides modular Meldrum's acid amine-reactive Michael acceptor (MaMa) molecules according to Formula A. The molecules herein may be used for a variety of purposes, such as probes, bioconjugation applications, etc. The MaMa molecules of the present invention are capable of reacting with an amine, creating a double amine molecule.

Formula A

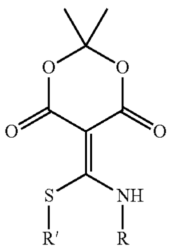

Chemistry well known to one of ordinary skill in the art allows for the attachment of a wide variety of molecules to R of Formula A, and the scope of the present invention includes said wide variety of molecules. Thus, the present invention provides a foundational molecule that can be easily functionalized for various purposes. Non-limiting examples of Formula A are disclosed herein and shown throughout the figures, for example in FIG. 2, FIG. 4, FIG. 6, and FIG. 11, FIG. 12, e.g., $CH_2)_2CH_3$. The present invention is in no way limited to the specific examples provided.

In certain embodiments, R is a bioorthogonal molecule. As used herein, the term "biorthogonal" refers to that which reacts in the presence of biological systems without cross-reacting with the biological systems. Thus, "biorthogonal" pairs, handles, molecules, etc. may be defined as reactive pairs that can react in the presence of biological systems without cross-reacting with the biological systems. Non-limiting examples of bioorthogonal handles include azides, alkynes, strained alkenes (norbornenes, trans-cyclooctenes), strained-alkynes (such as cyclooctyne derivatives), tetrazines, phosphines, etc.

In certain embodiments, R is an amino acid, e.g., a lysine residue. For example, in certain embodiments, R is an amino acid of a peptide. In some embodiments, R is a nucleotide, e.g., an oligonucleotide. In certain embodiments, the nucleotide is RNA, e.g., R is a strand of RNA. In certain embodiments, the nucleotide DNA, e.g., R is a strand of DNA. In some embodiments, R is a lipid. In some embodiments, R is a carbohydrate.

In certain embodiments, R is an alkyne (e.g., a terminal alkyne), an azide, a cyclic (strained) alkyne, a strained alkene, a tetrazine, or the like.

Figure 1:
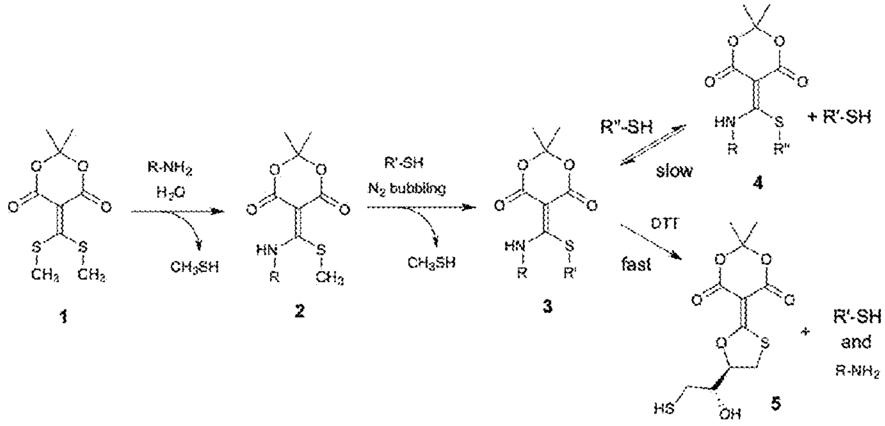
Figure 1:
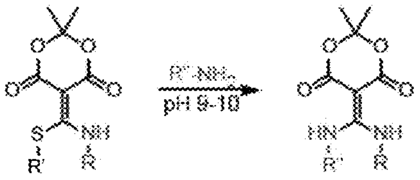
Figure 1:
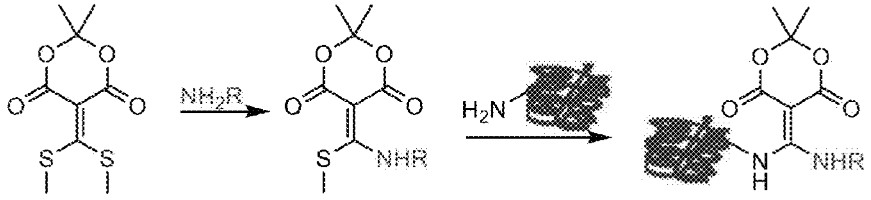

In certain embodiments, R is a label, such as a fluorophore. For example, an amine-containing fluorophore may be reacted with the precursor to Formula A (e.g., molecule (1) in FIG. 1) to create a fluorophore-containing molecule according to Formula A. Non-limiting examples of fluorophores include rhodamine, fluorescein, a fluorescein derivative, TAMRA, BDP, Cyanine3, Cyanine 5, Cyanine 7, a cadaverine derivative, a putrescin derivative, an AlexaFluor dye, or a DynaFluor dye. For example, Cyanine3 amine (having a free amino group) reacts with molecule (1) of FIG. 1, thus Cyanine3 becomes R in Formula A. Generally, the fluorophores that may be considered for R of Formula A may be fluorophores comprising a free amino group for reaction with molecule (1). However, the present invention is not limited to amino fluorophores. For example, in certain embodiments, a fluorophore may be attached via a linking moiety comprising a free amino group. In certain embodiments, R is a quencher, e.g., fluorescence quencher.

In certain embodiments, R is a tag. Non-limiting examples of tags include biotin or a biotin-derivative, a His tag, a FLAG tag, a Myc tag, a GST tag, an HA tag, an AviTag, a Strep tag, a V5 tag, and ALFA tag, a Spot tag, a T7 tag, an NE tag, a C tag, a calmodulin tag, a polyglutamate tag, a polyarginine tag, an E tag, a Rho tag, an S tag, an SBP tag, a Softag tag, a TC tag, a Ty tag, a VSV tag, an Xpress tag, a SNAP tag, a CLIP tag, a Halo tag, a BCCP tag, a glutathione transferase tag, a GFP tag, an HUH tag, a maltose binding protein tag, a Nus tag, a thioredoxin tag, an Fc tag, a CRDSAT tag, an imaging tag, a mass tag, or the like.

In some embodiments, R is a drug or a prodrug, e.g., a cytotoxic drug. Non-limiting examples of drugs include emtansine, ozogamicin, vedotin, and/or deruxtecan. The present invention is not limited to the aforementioned drugs and includes any amine-attachable drugs.

In some embodiments, R is a moiety for localizing the MaMa molecule to a particular location, e.g., a cellular location such as a particular organelle, a location within the organism, etc. For example, a triaryl phosphonium targets the mitochondria.

In certain embodiments, R is polyethylene glycol (PEG) or a substituted PEG. For example, in certain embodiments, R is a PEG-linked azide, alkyne (e.g., a terminal alkyne), a cyclic (strained) alkyne, a strained alkene, a tetrazine, or the like. In certain embodiments, R is a PEG-linked peptide. In certain embodiments, R is a PEG-linked solid support.

The MaMa molecules may be attached to a solid support via R, for various purposes such as protein purification, protein capture, surface plasmon resonance (SPR), etc. For example, in some embodiments, R is a resin, a plate, a slide a surface for SPR, etc. The MaMa molecules may be readily attached to the solid support using reactions with the thiol (see molecule (1), FIG. 1). Many commercially available solid supports are primed to provide the amine with which molecule (1) may react to form Formula A, wherein R is the solid support. For example, an SPR surface may feature free amines groups that can readily react with the MaMa precursor. Other technologies for which solid supports may be useful include atomic force microscopy (AFM).

In certain embodiments, the MaMa molecule can be attached to a surface via a tag. For example, in certain embodiments, R (or R') is biotin, which allows for attachment to an avid-labeled plate.

In some embodiments, R' is $CH_3$ (e.g., SR' is methane thiol, SMe); however, the present invention is not limited to methane thiol. In certain embodiments, R'=—$CH_3$, —$(CH_2)_nCH_3$, however, the present invention is not limited to alkanes.

In certain embodiments, R' is an amino acid, e.g., a lysine residue. For example, in certain embodiments, R' is an amino acid of a peptide. In some embodiments, R' is a nucleotide, e.g., an oligonucleotide. In certain embodiments, the nucleotide is RNA, e.g., R' is a strand of RNA. In certain embodiments, the nucleotide DNA, e.g., R' is a strand of DNA. In some embodiments, R' is a lipid. In some embodiments, R' is a carbohydrate.

In certain embodiments, R' is an alkyne (e.g., a terminal alkyne), an azide, a cyclic (strained) alkyne, a strained alkene, a tetrazine, or the like.

In certain embodiments, R' is a label, such as a fluorophore. For example, an amine-containing fluorophore may be reacted with the precursor to Formula A (e.g., molecule (1) in FIG. 1) to create a fluorophore-containing molecule according to Formula A. Non-limiting examples of fluorophores include rhodamine, fluorescein, a fluorescein derivative, TAMRA, BDP, Cyanine3, Cyanine 5, Cyanine 7, a cadaverine derivative, a putrescin derivative, an AlexaFluor dye, or a DynaFluor dye. For example, Cyanine3 amine (having a free amino group) reacts with molecule (1) of FIG. 1, thus Cyanine3 becomes R in Formula A. Generally, the fluorophores that may be considered for R of Formula A may be fluorophores comprising a free amino group for reaction with molecule (1). However, the present invention is not limited to amino fluorophores. For example, in certain embodiments, a fluorophore may be attached via a linking moiety comprising a free amino group.

In certain embodiments, R' is a quencher, e.g., fluorescence quencher.

In certain embodiments, R' is a tag. Non-limiting examples of tags include biotin or a biotin-derivative, a His tag, a FLAG tag, a Myc tag, a GST tag, an HA tag, an AviTag, a Strep tag, a V5 tag, and ALFA tag, a Spot tag, a T7 tag, an NE tag, a C tag, a calmodulin tag, a polyglutamate tag, a polyarginine tag, an E tag, a Rho tag, an S tag, an SBP tag, a Softag tag, a TC tag, a Ty tag, a VSV tag, an Xpress tag, a SNAP tag, a CLIP tag, a Halo tag, a BCCP tag, a glutathione transferase tag, a GFP tag, an HUH tag, a maltose binding protein tag, a Nus tag, a thioredoxin tag, an Fc tag, a CRDSAT tag, an imaging tag, a mass tag, or the like.

In some embodiments, R' is a drug or a prodrug, e.g., a cytotoxic drug. Non-limiting examples of drugs include emtansine, ozogamicin, vedotin, and/or deruxtecan. The present invention is not limited to the aforementioned drugs and includes any amine-attachable drugs.

In some embodiments, R' is a moiety for localizing the MaMa molecule to a particular location, e.g., a cellular location such as a particular organelle, a location within the organism, etc. For example, a triaryl phosphonium targets the mitochondria.

In certain embodiments, R' is polyethylene glycol (PEG) or a substituted PEG. For example, in certain embodiments, R' is a PEG-linked azide, alkyne (e.g., a terminal alkyne), a cyclic (strained) alkyne, a strained alkene, a tetrazine, or the like. In certain embodiments, R' is a PEG-linked peptide. In certain embodiments, R' is a PEG-linked solid support.

In certain embodiments, R' is a moiety that allows for selectivity, e.g., for localization, for specificity with respect to which molecules the MaMa molecule will react with, etc.

In some embodiments, both R and R' are fluorophores. Such a molecule may be useful for assays, for example assays that detect dissociation of the two fluorophores, e.g., when the reaction with the amine of interest occurs.

The MaMa molecules may be attached to a solid support via R', for various purposes as discussed above. For example, in some embodiments, R' is a resin, a plate, a slide a surface for SPR, etc.

As previously discussed, the MaMa compounds of the present invention, e.g., according to Formula A, can react with amines. An example of an amine with which Formula A can react includes but is not limited to lysine. In certain embodiments, the amine is a lysine derivative. Other non-limiting examples of amines that may react with the MaMa molecules of the present invention include amines according to R"NH or R"$NH_2$, e.g., R"$(CH_2)_nNH_2$, e.g., $CH_3NH_2$, $CH_3(CH_2)_nNH_2$, (e.g., propyl amine ($CH_3(CH_2)_2NH_2$), ethyl amine ($CH_3CH_2NH_2$)), $CH_3$(CHR")$_n(CH_2)_nNH_2$, or $CH_3(CH_2)_n$(CH R")$_nNH_2$, etc. Referring to the formulas above, in some embodiments n=1, 2, 3, 4, 5, 6, 7, 8, 9, 10, 11, 12, 13, 14, 15, 16, 17, 18, 19, 20, or more than 20. The present invention is not limited to the aforementioned examples of lysine and R"N, R"NH, and R"$NH_2$.

In certain embodiments, the amine is that of a protein molecule. In certain embodiments, the amine is that of a solid support.

In certain embodiments, R" is an amine-linked molecule, e.g., not necessarily a protein but a molecule comprising an amine. For example, in some embodiments, R" is an amine-linked nucleotide. In certain embodiments, R" is an amine fluorophore. In some embodiments, R" is an amine-linked polymer, e.g., an amine linked epoxy polymer.

The present invention is not limited to biopolymers; conventional polymers may be considered for R, R', and R".

As previously discussed, the MaMa molecule can react with lysine of a particular protein or peptide. In certain embodiments, the protein or peptide is an enzyme, an antibody or fragment thereof, a cell-surface protein, a receptor, a hormone or neurotransmitter, (e.g., insulin), designer proteins, immunoglobulin-binding proteins (e.g., protein A or derivatives or conjugates thereof, Protein G or derivatives or conjugates thereof, Protein A/G or derivatives or conjugates thereof, Protein L or derivatives or conjugates thereof, the like), a structural protein (e.g., collagen, elastin, etc.), etc. In certain embodiments, the protein or peptide is a mammalian protein, a non-mammalian animal protein (e.g., fish, bird, amphibian protein), a viral protein, a bacterial protein, a fungal protein, a parasitic protein, a protozoan protein, etc. The present invention is not limited to any particular protein or amine compound, and includes other molecules featuring amine moieties, e.g., amino-oligonucleotides, amino-modified DNA, amino-containing sugars, amino-containing lipids, etc.

As previously discussed, the MaMa compounds according to Formula A can react with an amine (e.g., lysine) as described above and undergo substitution chemistry whereby the thiol SR is eliminated from the molecule. This yields compositions according to Formula B below, a double amine adduct.

Formula B

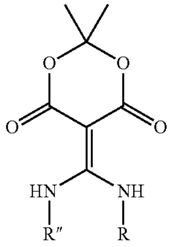

Figure 2:
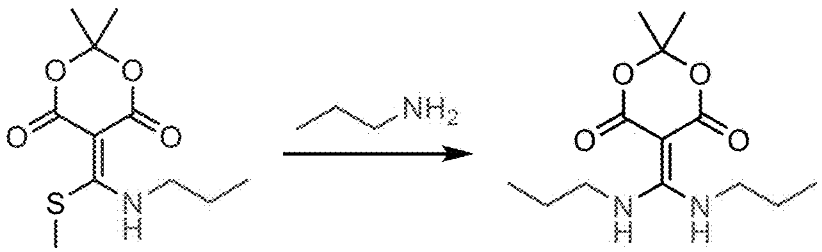
Figure 2:
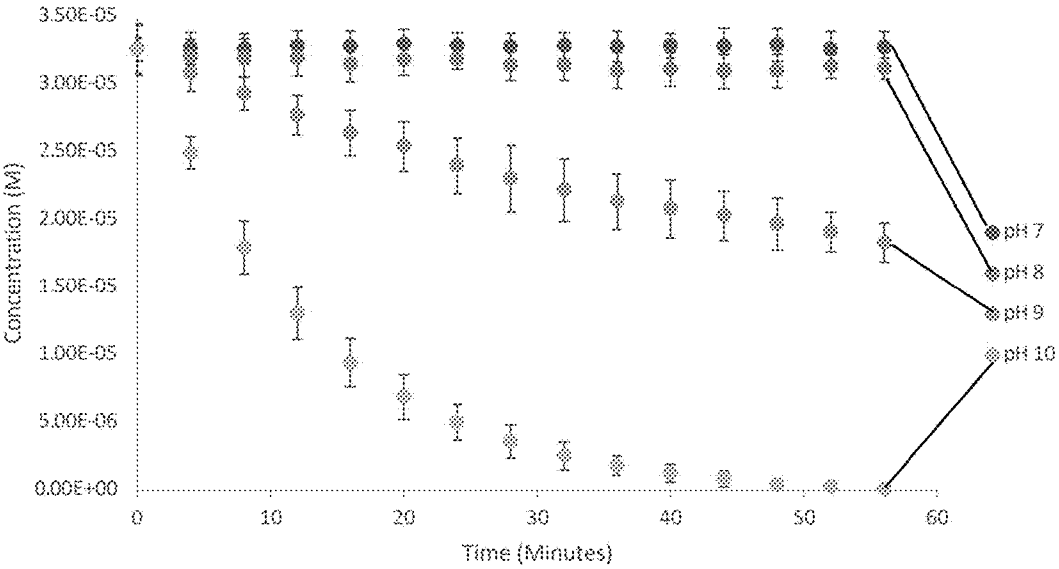

FIG. 2 shows the schematic conversion of a single amine adduct (MaMa molecule (2)) to a double amine adduct (molecule (3)) (double amine molecule). The concentration of (2) relative to the conversion of (2) to (3) at various pH (7-10) over the course of 60 minutes is shown. The data shows a pH dependent conversion of (2) to (3).

Figure 3:
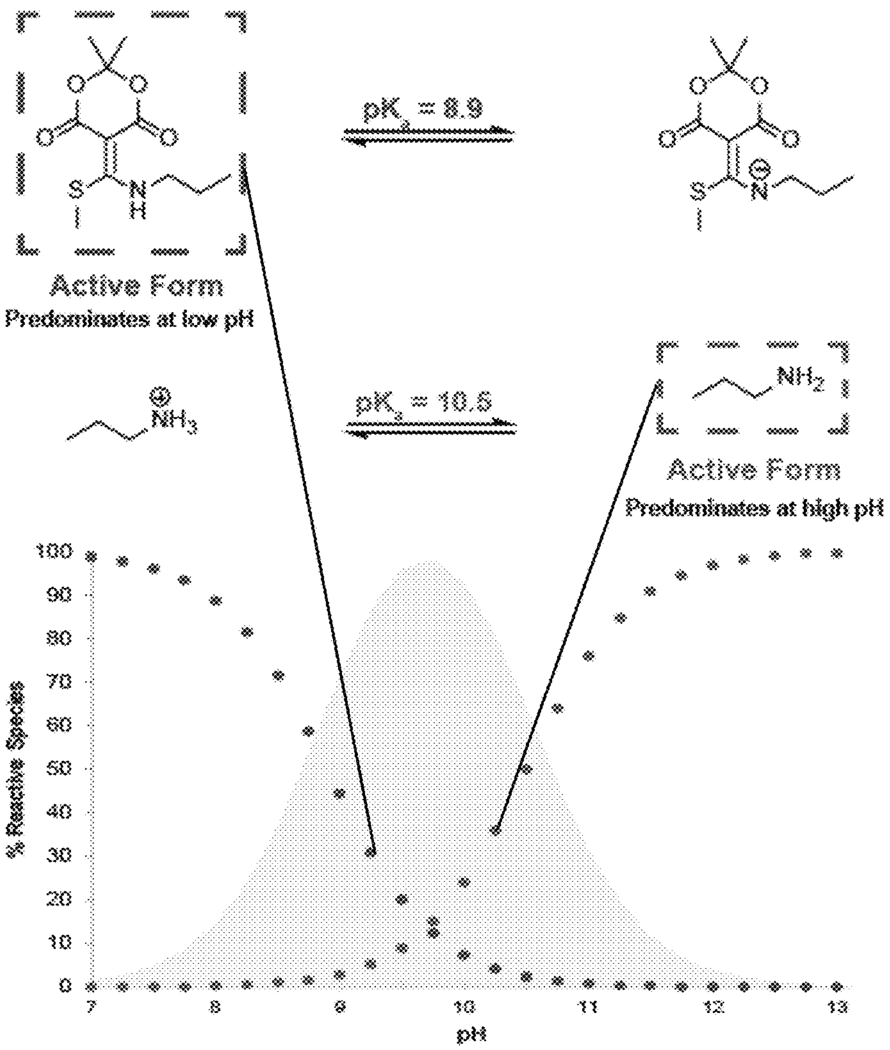
Figure 4A:
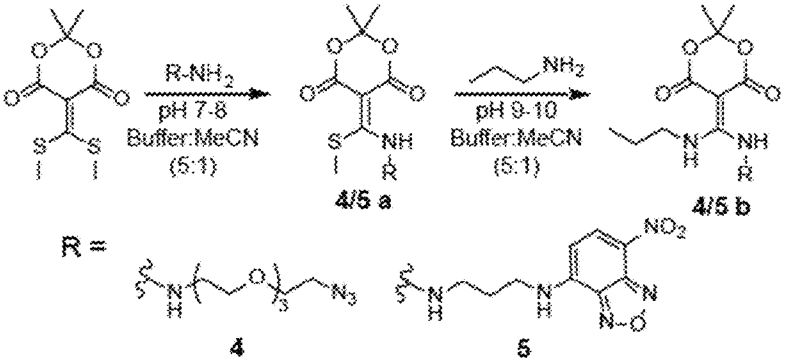
FIG. 4A shows the general synthesis of MaMa functional analogs (azide and NBD) and their respective controls. The present invention is not limited to the MaMa molecules in FIG. 4A nor the reaction conditions described.
Figure 4A:
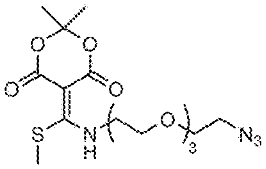
Figure 4A:
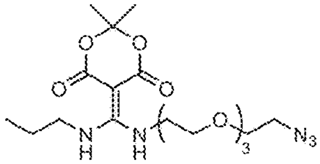
Figure 4A:
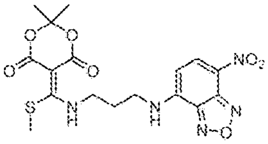
Figure 4A:
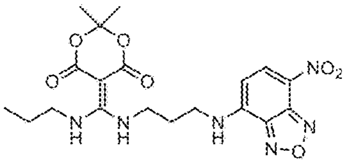
Figure 4B:
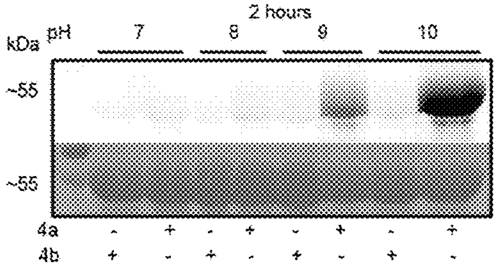
FIG. 4B shows an SDS-gel of BSA treated with (4a) and (4b) (shown in FIG. 4A) at pH 7-10 after 2 hours and being treated with a Cy3 cyclooctyne (DBCO).
Figure 4C:
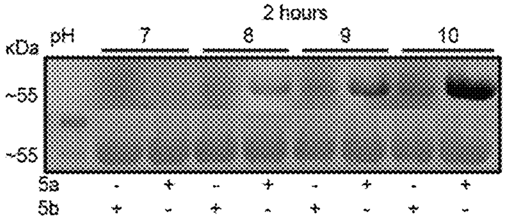
FIG. 4C shows an SDS-gel of BSA treated with (5a) and (5b) (shown in FIG. 4A) at pH 7-10 after 2 hours.

The optimal pH at which to react the MaMa molecule and the amine may generally be dependent upon the $pK_a$ of the MaMa molecule (electrophile) and the $pK_a$ of the amine (nucleophile). As an example, FIG. 3 shows the equilibrium of the single amine adduct existing in the active neutral form and the unreactive anionic form upon deprotonation, as well as the equilibrium of propyl amine in its unreactive protonated form and its nucleophilic neutral form. The plot shows the relative reactive species of the neutral single amine adduct and the neutral propyl amine as a function of pH, overlaid with an optimal reactivity curve. The present invention is not bound by any theory related to the optimal reactivity curve.

In certain embodiments, for the purpose of the reaction, the MaMa molecule is an aqueous solution having a pH that is within 30% of its $pK_a$. In certain embodiments, for the purpose of the reaction, the MaMa molecule is an aqueous solution having a pH that is within 20% of its $pK_a$. In certain embodiments, for the purpose of the reaction, the MaMa molecule is an aqueous solution having a pH that is within 10% of its $pK_a$.

In certain embodiments, for the purpose of the reaction, the MaMa molecule and amine are an aqueous solution having a pH that is within 30% of the $pK_a$ of the MaMa molecule and within 30% of the $pK_a$ of the amine. In certain embodiments, for the purpose of the reaction, the MaMa molecule and amine are an aqueous solution having a pH that is within 20% of the $pK_a$ of the MaMa molecule and within 20% of the $pK_a$ of the amine. In certain embodiments, for the purpose of the reaction, the MaMa molecule and amine are an aqueous solution having a pH that is within 10% of the $pK_a$ of the MaMa molecule and within 10% of the $pK_a$ of the amine.

In certain embodiments, the MaMa molecule (e.g., the compound according to Formula A) reacts with the amine in an aqueous solution having a pH of 7 or greater, e.g., a pH from 7-8. In certain embodiments, the MaMa molecule (e.g., the compound according to Formula A) reacts with the amine in an aqueous solution having a pH of 8 or greater, e.g., 8-9. In certain embodiments, the MaMa molecule (e.g., the compound according to Formula A) reacts with the amine in an aqueous solution having a pH of 9 or greater, e.g., 9-10. In certain embodiments, the MaMa molecule (e.g., the compound according to Formula A) reacts with the amine in an aqueous solution having a pH of 10 or greater, e.g., 10-11. In certain embodiments, the MaMa molecule (e.g., the compound according to Formula A) reacts with the amine in an aqueous solution having a pH of 11 or greater, e.g., 11-12. In certain embodiments, the MaMa molecule (e.g., the compound according to Formula A) reacts with the amine in an aqueous solution having a pH of 12 or greater.

As discussed above, the double amine addition reaction is dependent upon the $pK_a$ of the MaMa molecule (electrophile) as well as the $pK_a$ of the amine (nucleophile) and the microenvironment of the molecule may allow for the reaction to occur regardless of the pH of the aqueous solution. Thus, the present invention is not limited to reactions in an aqueous solution having a pH of 7 or greater, e.g., 8, 9, 10, etc. In certain embodiments, the MaMa molecule reacts with the amine in a solution having a pH from 6-7. In certain embodiments, the MaMa molecule reacts with the amine in a solution having a pH from 5-6. In certain embodiments, the MaMa molecule reacts with the amine in a solution having a pH from 4-5. In certain embodiments, the MaMa molecule reacts with the amine in a solution having a pH from 3-4. In certain embodiments, the MaMa molecule reacts with the amine in a solution having a pH from 2-3.

The MaMa molecules of the present invention may be designed for the chemical or biochemical environments in which they are needed.

In some embodiments, the addition to the double amine reaction occurs within 15 minutes. In some embodiments, the reaction occurs within 30 minutes. In some embodiments, the reaction occurs within 1 hour. In some embodiments, the reaction occurs within 2 hours. In some embodiments, the reaction occurs within 3 hours. In some embodiments, the reaction occurs within 6 hours. In some embodiments, the reaction occurs within 12 hours. In some embodiments, the reaction occurs in less than 1 hour. In some embodiments, the reaction occurs in less than 2 hours. In some embodiments, the reaction occurs in less than 3 hours. In some embodiments, the reaction occurs in less than 6 hours. In some embodiments, the reaction occurs in less than 12 hours.

The MaMa molecules of the present invention are uniquely stable as compared with other amine-reactive bioconjugation reagents. For example, the MaMa molecules can form reversible hydroxylates at high pH, which helps prevent breakdown of the compound. (Note that the reaction between the MaMa molecule and an amine (e.g., lysine residue) is faster than hydroxylate formation.) Without wishing to limit the present invention to any theory or mechanism, it is believed that the ability of the MaMa molecule to form the hydroxylate helps allow the MaMa molecule to exist in aqueous stock solutions for prolonged time periods (prior to its reaction with an amine) without risk of hydrolytic degradation.

In certain embodiments, the MaMa molecules are stable in an aqueous solution having a neutral pH for a period of time. In certain embodiments, the MaMa molecules are stable in an aqueous solution having a pH from 7-8 for a period of time. In certain embodiments, the MaMa molecules are stable in an aqueous solution having a pH from 8-9 for a period of time. In certain embodiments, the MaMa molecules are stable in an aqueous solution having a pH from 9-10 for a period of time. In certain embodiments, the MaMa molecules are stable in an aqueous solution having a pH from 10-11 for a period of time. In certain embodiments, the MaMa molecules are stable in an aqueous solution having a pH from 11-12 for a period of time. In certain embodiments, the MaMa molecules are stable in an aqueous solution having a pH of 7 or greater for a period of time. In certain embodiments, the MaMa molecules are stable in an aqueous solution having a pH of 8 or greater for a period of time. In certain embodiments, the MaMa molecules are stable in an aqueous solution having a pH of 9 or greater for a period of time. In certain embodiments, the MaMa molecules are stable in an aqueous solution having a pH of 10 or greater for a period of time. In certain embodiments, the MaMa molecules are stable in an aqueous solution having a pH of 11 or greater for a period of time. In certain embodiments, the MaMa molecules are stable in an aqueous solution having a pH of 12 or greater for a period of time. The period of time may be, for example, 1 day, 2 days, 7 days, 10 days, 30 days, 60 days, 2 months, 6 months, 1 year, 2 years, 3 years, at least 1 day, at least 2 days, at least 7 days, at least 10 days, at least 30 days, at least 60 days, at least 2 months, at least 6 months, at least 1 year, at least 2 years, at least 3 years, etc.

As previously discussed, the MaMa molecules herein may be used for a variety of purposes. For example, the MaMa molecules may be used as probes for labeling of protein, or for bioconjugation applications, as protein-fluorophore conjugates, as protein drug conjugates, etc. The modular nature of the first amine addition allows for the production of probes with a range of commercially available amine-containing fluorophores, natural products, or even radioisotopes.

Figure 7:
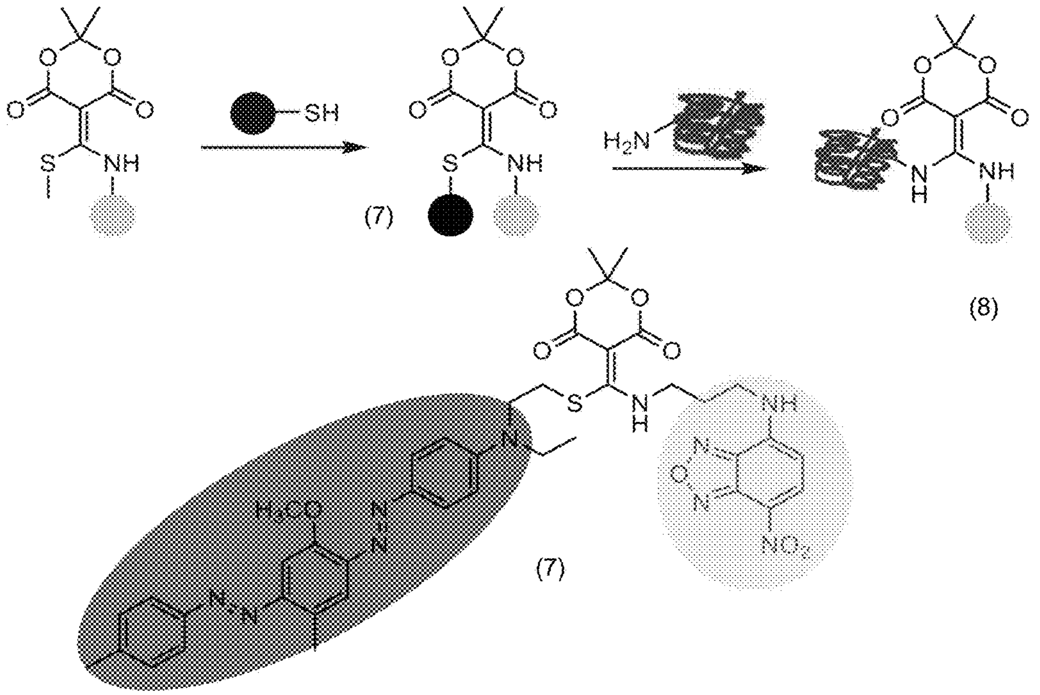
FIG. 7 shows a non-limiting example of a fluorophore-quencher pair (7). The fluorescence quencher dissociates from the molecule upon conjugation to lysine residues (or other amines), generating a MaMa molecule that is fluorogenic (8).
Figure 8:
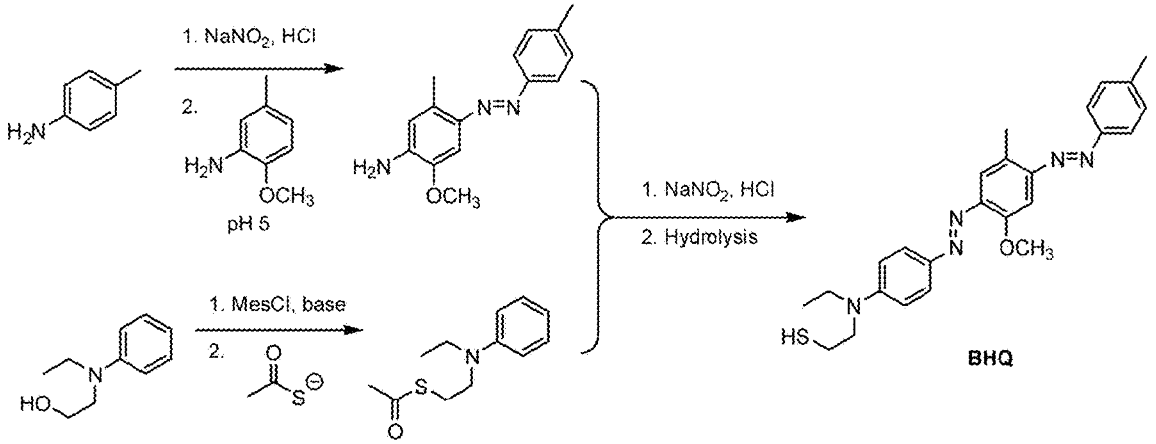
FIG. 8 shows synthesis of the fluorophore in FIG. 7.
Figure 9:
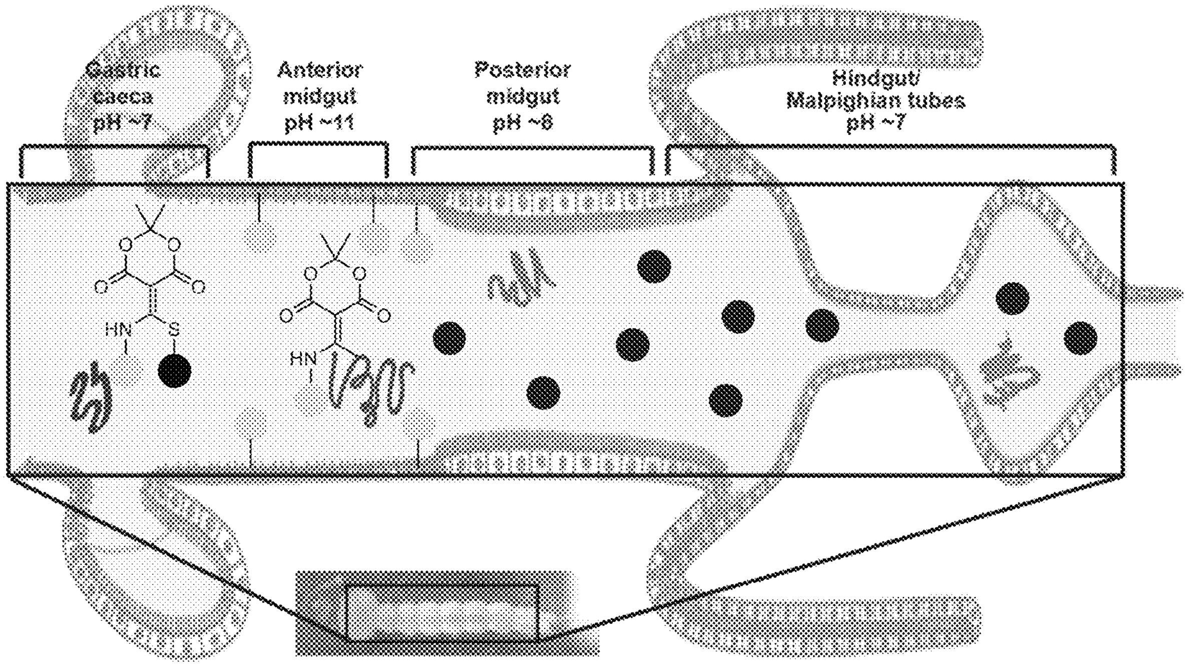
FIG. 9 shows a non-limiting example of an application of the fluorogenic MaMa wherein mosquito larva are covalently modified (and fluorescently labeled) only in regions with high pH.

As an example, in certain embodiments, the MaMa molecule comprises a fluorophore-quencher pair (see FIG. 7, FIG. 8). The fluorescence quencher dissociates from the molecule upon conjugation to lysine residues (or other amines), generating a MaMa molecule that is fluorogenic. An example of the application of the fluorogeneic MaMa molecule is shown in FIG. 9, wherein mosquito larva are covalently modified (and fluorescently labeled) only in regions with high pH.

The present invention generally provides a method of producing a double amine molecule in an aqueous solution, e.g., a composition according to Formula B. The method comprises introducing an amine to a MaMa molecule, e.g., a composition according to Formula A. The MaMa molecule reacts with the amine to form a double amine molecule, e.g., a composition according to Formula B. In some embodiments, the amine is that of a lysine molecule, e.g., of a protein.

In some embodiments, the aqueous solution has a pH that is within 20% of a $pK_a$ of the MaMa molecule (e.g., the composition according to Formula A) and within 20% of a $pK_a$ of the amine. In some embodiments, the aqueous solution has a pH that is within 10% of a $pK_a$ of the MaMa molecule (e.g., the composition according to Formula A) and within 10% of a $pK_a$ of the amine. In some embodiments, the aqueous solution has a pH that is 8 or greater. In some embodiments, the aqueous solution has a pH that is 9 or greater. In some embodiments, the aqueous solution has a pH that is 10 or greater.

In some embodiments, the double amine molecule (e.g., the composition according to Formula B) is produced within 1 hour. In some embodiments, the double amine molecule (e.g., the composition according to Formula B) is produced within 2 hours. In some embodiments, the double amine molecule (e.g., the composition according to Formula B) is produced within 6 hours.

The present invention also provides more specific methods of labelling a protein. In certain embodiments, the method comprises introducing a MaMa molecule of the present invention to the protein, wherein the MaMa molecule comprises a label. The MaMa molecule reacts with and binds to a lysine residue of the protein to bind the label to the protein.

In certain embodiments, the MaMa molecule comprises a fluorophore, e.g., R is a fluorophore, e.g., derived from an amine-containing fluorophore. Non-limiting examples of fluorophores includes rhodamine, a fluorescein derivative, TAMRA, BDP, Cyanine3, Cyanine 5, Cyanine 7, a cadaverine derivative, a putrescin derivative, an AlexaFluor dye, and a DynaFluor dye, and others disclosed herein.

In certain embodiments, the R is a fluorophore and R' is a quencher. The present invention is not limited to fluorophores. In certain embodiments, R is an amine-containing label, for example an amine containing a quantum dot.

The present invention also provides methods of preparing a protein for purification. For example, a MaMa molecule may be produced such that R comprises a purification-associated tag. The MaMa molecule, when it reacts with and binds to lysine residues of the protein, attaches the purification associated tag to the protein. Non-limiting examples of purification tags include a His tag, FLAG tag, Myc tag, GST tag, HA tag, AviTag, Strep tag, or a V5 tag, and others described herein.

The present invention also provides methods of preparing a protein for imaging (e.g., live imaging in a biological system). For example, a MaMa molecule may be produced such that R comprises an imaging associated tag. The MaMa molecule, when it reacts with and attaches to lysine residues of the protein, attaches the imaging associated tag to the protein.

Figure 10:
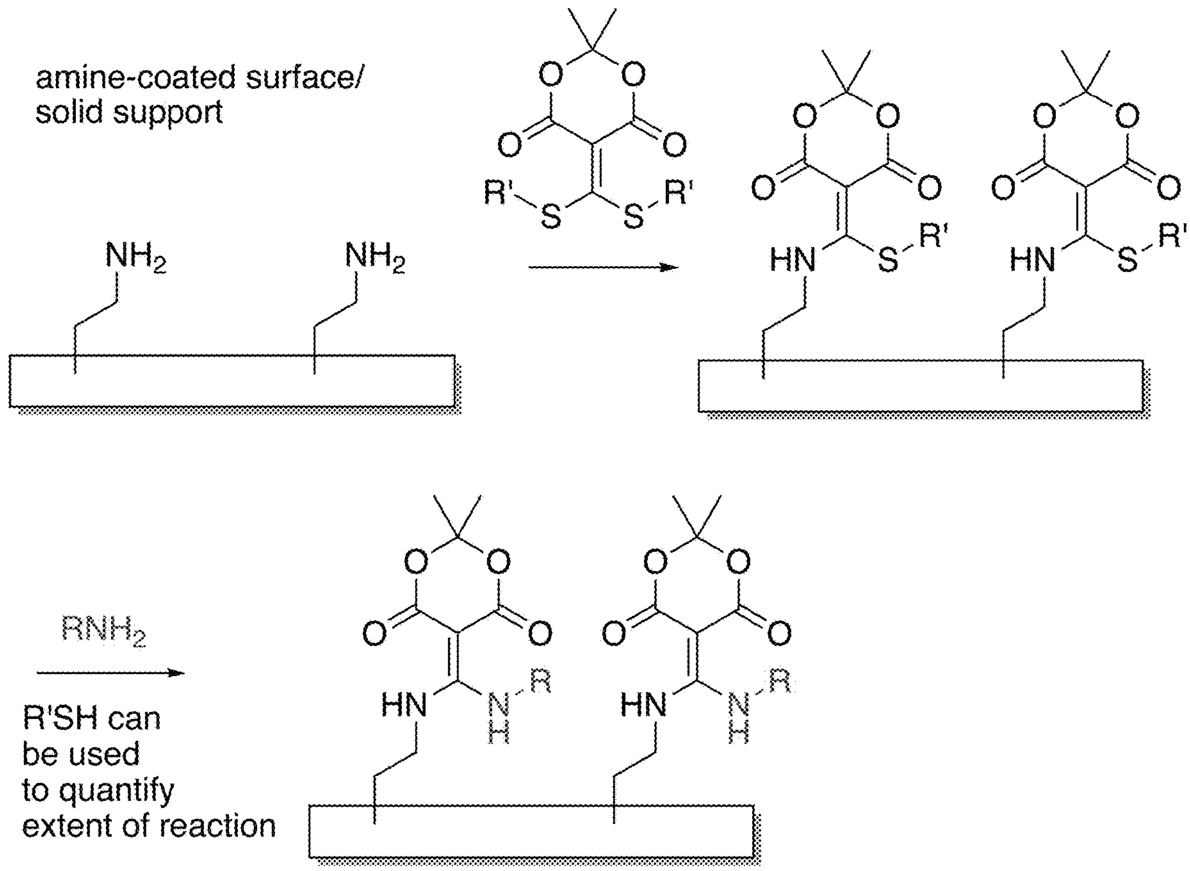
FIG. 10 shows an example of the attachment of a MaMa molecule to an amine-coated surface or solid support.

The present invention also provides systems wherein MaMa molecules are bound to a surface, e.g., a plate (e.g., a microplate), a resin, etc. These systems may be used for isolating or capturing proteins, or for other purposes. For example, a solution comprising protein (e.g., a protein of interest) may be introduced to the MaMa-surface system where the protein reacts with and binds to the MaMa molecules bound to the surface, thereby linking the protein to the surface. FIG. 10 shows an example of the attachment of a MaMa molecule to an amine-coated surface or solid support. The MaMa precursor (SR' and SR', for example) reacts with an amine-coated surface, thereby attaching to the surface. The remaining SR' group is free to react with an amine (e.g., $RNH_2$). In certain embodiments, R'SH can be used to quantify the extent of the reaction with the amine.

The present invention also provides kits comprising one or more compositions disclosed herein. For example, the present invention provides kits comprising a composition according to Formula A in solution. In certain embodiments, the kit is for the purpose of labeling a protein. In certain embodiments, the composition in the kit is shelf stable for at least 1 week. In certain embodiments, the composition in the kit is shelf stable for at least 2 weeks. In certain embodiments, the composition in the kit is shelf stable for at least 3 weeks. In certain embodiments, the composition in the kit is shelf stable for at least 1 month. In certain embodiments, the composition in the kit is shelf stable for at least 6 months. In certain embodiments, the composition in the kit is shelf stable for at least 12 months.

Figure 11:
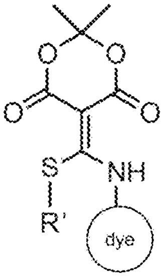
FIG. 11 shows non-limiting examples of MaMa compositions of the present invention.
Figure 11:
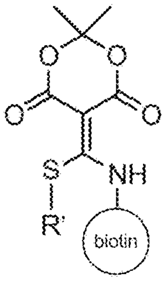
Figure 11:
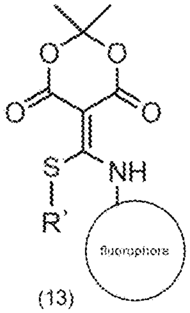
Figure 11:
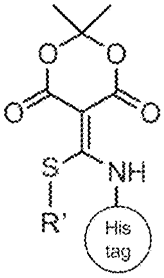
Figure 11:
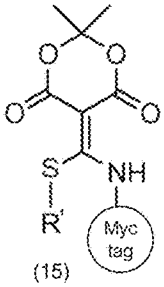
Figure 11:
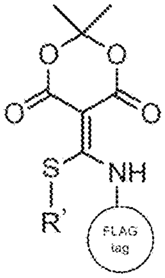
Figure 11:
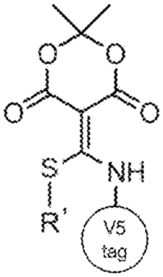
Figure 11:
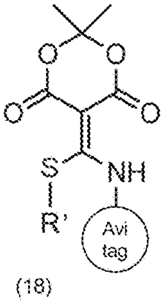
Figure 11:
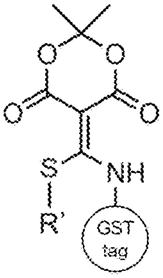
Figure 11:
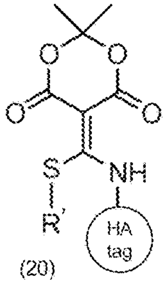
Figure 11:
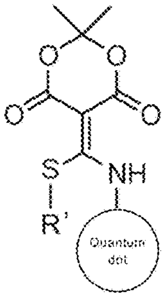
Figure 11:
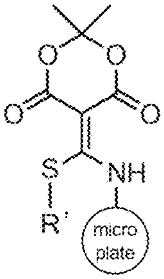
Figure 11:
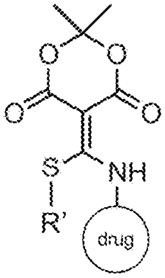
Figure 11:
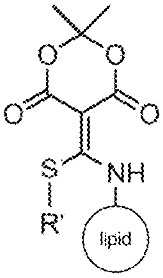
Figure 11:
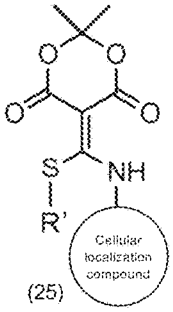
Figure 11:
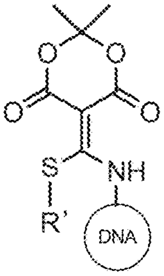
Figure 11:
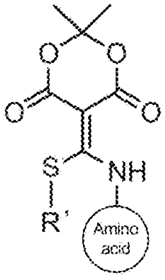
Figure 11:
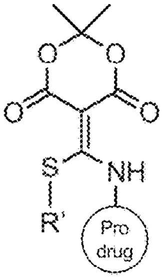
Figure 11:
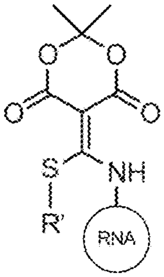
Figure 11:
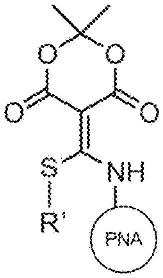
Figure 12:
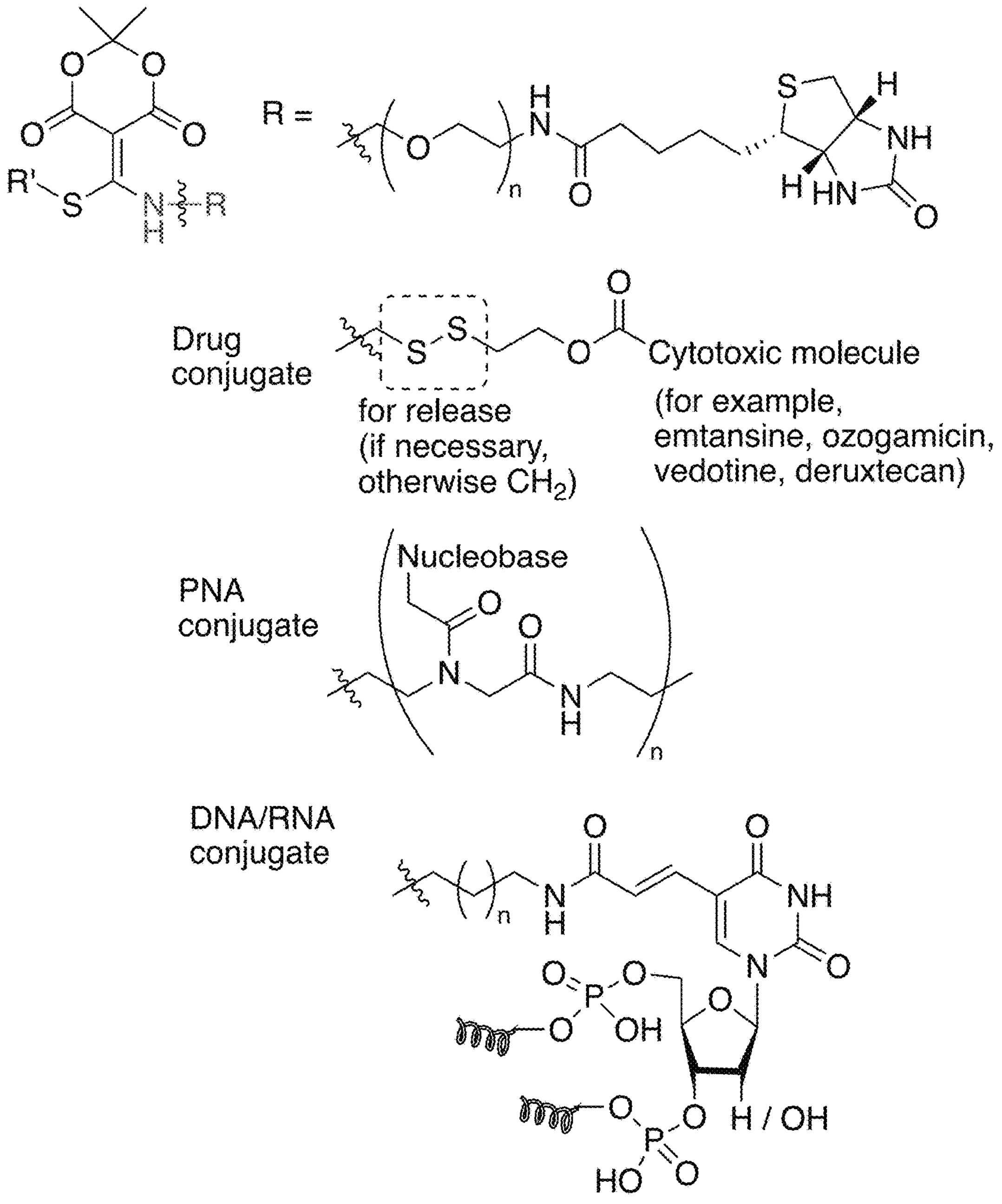
FIG. 12 shows non-limiting examples of the molecules in FIG. 11, e.g., a MaMa molecule linked to a drug, a DNA/RNA molecule, a PNA molecule.

The present invention is not limited to the particular examples of R described herein. Additional non-limiting examples of MaMa molecules of the present invention are shown in FIG. 11 and FIG. 12. Note that it is within the scope of the invention to replace the specific R groups disclosed herein with others not specifically listed but that can be chemically added to the MaMa precursor. Such reactions are well known to one of ordinary skill in the art.

Example 1

The following is a non-limiting example of the present invention. It is to be understood that said example is not intended to limit the present invention in any way. Equivalents or substitutes are within the scope of the present invention.

Referring to FIG. 2, it was shown that a 1:1 ratio of (1) (shown in FIG. 1) to free amine in buffer garners a single substituted product (2) at a range of pH values. With an excess of free amine in buffer, a double amine conjugation forms (3). Without wishing to limit the present invention to any theory or mechanism, it is believed that aggregation that was seen was due to the crosslinking of two lysine residues to the same electrophile, resulting in oligomers, e.g., the double amine probe (3) is no longer reactive to DTT, cysteine, and other reducing agents, rendering this an irreversible reaction. This led to the development of a new class of lysine probes.

The addition of amine to MaMa was observed at a range of pH values, and their rates were studied to optimize utility for the conjugation reaction. The second addition of propyl amine to (3) was monitored via UV-Vis, following the disappearance of a unique starting material peak. Data showed a pH dependence on this reaction, being fastest at pH 10, and very slow at pH 7 and pH 8 (FIG. 2). At pH 9 and 10, this addition appeared to have followed second order kinetics. It was hypothesized that in order for the reaction to occur, both the nucleophilic amine and electrophilic MaMa may need to exist in neutral forms. When a Henderson-Hasselbalch analysis was used (utilizing the reported $pK_a$ of the N—H bond in MaMa=8.9 and propyl ammonium=10.5) to calculate percent composition of nucleophile and electrophile as a function of pH, a picture emerged of the reactivity profile for these probes (see FIG. 3A, FIG. 3B, and FIG. 3C). When these are treated as concentrations and multiplied, a rate profile emerged showing the optimal rate to be found at around pH 9.8. To measure the rate at pH 10 the reaction under pseudo-first order conditions was followed, and the second-order kinetic rate was found to be 0.14+/−0.02 $M^{-1}s^{-1}$.

The data shows double addition reactivity, rendering the molecules advantageous in the highly modular synthesis of new bioconjucation probes. This led to the development of a library of MaMa probes, including but not limited to PEG azide (4a), and a nitrobenzoxadiazole (NBD) fluorophore derivative (5a) (see FIG. 4A). Synthesis of these compounds resulted from the corresponding free amine to 1 in pH 7 buffer at a 1:1 ratio. Most of the reactions proceeded in nearly quantitative yield, providing the pure products after simple acetone extraction. Control compounds of each of these probes were synthesized by reacting the respective single adducts with propyl amine at pH 10 ((4b) and (5b) respectively).

Utilizing bovine serum albumin (BSA) as a non-limiting example, the utility of these compounds for protein labeling was tested at a range of pH 7-10. Covalent modification of BSA was analyzed via SDS-PAGE electrophoresis and the labeling results were consistent with the small molecule kinetic data and the understanding of the reactivity. Control compounds showed minimal labeling of BSA across the tested pH range, confirming their inability to covalently modify proteins. Reactive compounds showed negligible labeling at pH 7 but increased labeling from pH 8 up to pH 10 after 2 hours (see FIG. 3B, FIG. 3C). Longer time point studies (e.g., 18 hours, 22 hours) showed more labeling at the lower pH, but minimal background. The presence of the azide was confirmed using a cyclooctyne fluorophore (Cy3-DBCO). The present invention is not limited to labeling of BSA.

Figure 5:
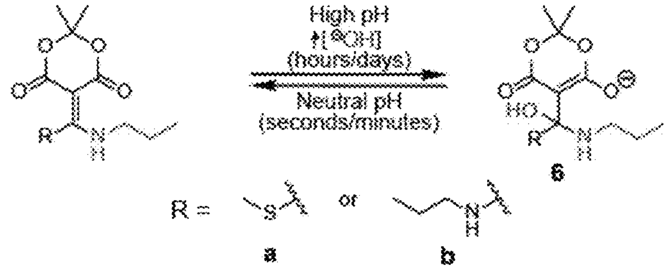
FIG. 5 shows a tetrahedral hydroxylate intermediate hypothesized to form at high pH over extended periods of time. Neutralization causes quick reversion, showing reversibility of hydrolytic product.
Figure 6:
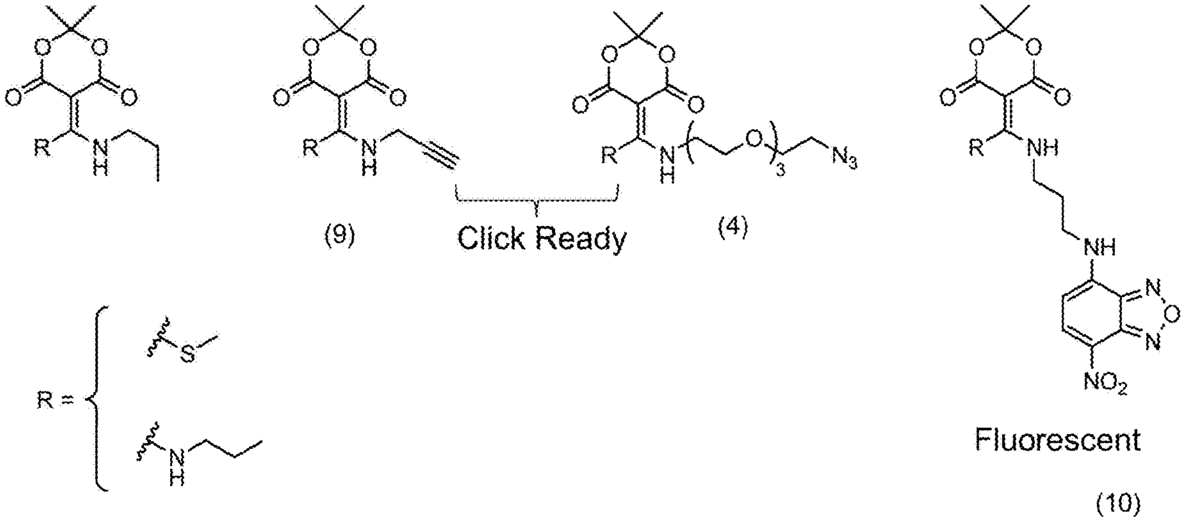
FIG. 6 shows additional non-limiting examples of MaMa molecules of the present invention.

UV/vis data had suggested that an unspecified change occurred on compounds over prolonged exposure to high pH in the absence of amines, but an NMR experiment helped to clarify. Over 42 hours, (2) slowly disappeared and in its place a set of peaks with similar relative integration grew in. Interestingly, the molecule did not appear to be falling apart, and it was hypothesized that it might be existing as the anionic hydroxylate (6a) (see FIG. 5). Furthermore, when the solution was neutralized, (2) was immediately restored. At pH 7, (6) is not formed, even at 24 hours, and the molecule appears to be stable. Additionally, (3) shows similar stability, with nothing occurring at pH 7, but the appearance of a hydroxylate (6b) occurs overtime at pH 12. Notably, the rate of reaction between MaMa and lysine residues is much faster than that of the hydroxylate formation. Without wishing to limit the present invention to any theory or mechanism, it is believed that this protective feature of the probe bolsters its utility for bioconjugations, as it can exist in aqueous stock solution for prolonged times prior to exposure to amines. Additionally, (3) was subjected to acidic conditions (pH 2) for 24 hours, but no changes to the structure were noted.

To test the stability of the fully conjugated adduct (double amine adduct) to various nucleophiles, including DTT and cysteine, the double-propyl scaffold was treated with 1 equivalent of DTT or cysteine at both pH 7 and 10. Subsequent NMR showed that (3) was stable after 24 hours of treatment at either pH. This observation was consistent with previous observations of irreversibility on proteins (under the conditions tested).

The MaMa analogs of the present invention can be designed for the chemical or biochemical environments in which they are needed. Moreover, the highly modular nature of the first amine addition lends this system to rapid probe development with a range of commercially available amine-containing fluorophores, natural products, or even radioisotopes. These compounds are a new tool in the bioconjugation tool chest, and enhance the scope of what is possible with lysine modification.

Embodiments of the present invention can be freely combined with each other if they are not mutually exclusive.

Although there has been shown and described the preferred embodiment of the present invention, it will be readily apparent to those skilled in the art that modifications may be made thereto which do not exceed the scope of the appended claims. Therefore, the scope of the invention is only to be limited by the following claims. In some embodiments, the figures presented in this patent application are drawn to scale, including the angles, ratios of dimensions, etc. In some embodiments, the figures are representative only and the claims are not limited by the dimensions of the figures. In some embodiments, descriptions of the inventions described herein using the phrase "comprising" includes embodiments that could be described as "consisting essentially of" or "consisting of", and as such the written description requirement for claiming one or more embodiments of the present invention using the phrase "consisting essentially of" or "consisting of" is met.

The reference numbers recited in the below claims are solely for ease of examination of this patent application, and are exemplary, and are not intended in any way to limit the scope of the claims to the particular features having the corresponding reference numbers in the drawings.

What is claimed is:

1. A kit comprising: a composition according to Formula A in aqueous solution; and a set of instructions or access thereto for reacting the composition according to Formula A with an amine to produce a stable double amine adduct;

Formula A

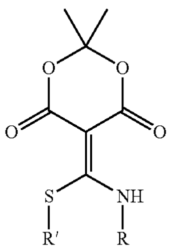

wherein R is an azide, or a tetrazine; and wherein R' is —$CH_3$ or an alkyl group.

2. The kit of claim 1, wherein the aqueous solution has a pH of 7 or greater.

3. The kit of claim 1 further comprising a reaction solution, the reaction solution having a pH of within 20% of a $pK_a$ of the composition according to Formula A.

* * * * *